(12) United States Patent
Mitsuzuka et al.

(10) Patent No.: US 10,455,951 B2
(45) Date of Patent: Oct. 29, 2019

(54) CUSHIONING MATERIAL HAVING SENSOR, AND BED

(71) Applicants: MITSUI CHEMICALS, INC., Tokyo (JP); A SCHOOL CORPORATION KANSAI UNIVERSITY, Osaka (JP)

(72) Inventors: Masahiko Mitsuzuka, Yokohama (JP); Satoshi Yamasaki, Chiba (JP); Yoshiro Tajitsu, Suita (JP)

(73) Assignees: MITSUI CHEMICALS, INC., Tokyo (JP); A SCHOOL CORPORATION KANSAI UNIVERSITY, Osaka (JP)

( * ) Notice: Subject to any disclaimer, the term of this patent is extended or adjusted under 35 U.S.C. 154(b) by 0 days.

(21) Appl. No.: 15/547,996

(22) PCT Filed: Feb. 5, 2016

(86) PCT No.: PCT/JP2016/053563
§ 371 (c)(1),
(2) Date: Aug. 1, 2017

(87) PCT Pub. No.: WO2016/125904
PCT Pub. Date: Aug. 11, 2016

(65) Prior Publication Data
US 2018/0020841 A1 Jan. 25, 2018

(30) Foreign Application Priority Data
Feb. 5, 2015 (JP) .................. 2015-020948

(51) Int. Cl.
*A47C 31/00* (2006.01)
*A47C 27/00* (2006.01)
(Continued)

(52) U.S. Cl.
CPC ............ *A47C 31/00* (2013.01); *A47C 27/002* (2013.01); *A61B 5/0082* (2013.01);
(Continued)

(58) Field of Classification Search
CPC ....... A47C 31/00; A47C 27/002; A47C 17/04; A61B 5/0082; A61B 5/1117;
(Continued)

(56) References Cited

U.S. PATENT DOCUMENTS 5,917,180 A * 6/1999 Reimer ..................... G01L 1/24
250/227.14
2006/0152378 A1 7/2006 Lokhorst
(Continued)

FOREIGN PATENT DOCUMENTS

JP 2009-022567 2/2009
JP 2012-193293 10/2012
(Continued)

OTHER PUBLICATIONS

International Preliminary Report on Patentability dated Aug. 17, 2017 filed in PCT/JP2016/053563, total 13 pages.
(Continued)

*Primary Examiner* — Robert G Santos
*Assistant Examiner* — Rahib T Zaman
(74) *Attorney, Agent, or Firm* — Rankin, Hill & Clark LLP

(57) ABSTRACT

The cushioning material having a sensor 1 includes a resin sheet 4 composed of photoelastic resin, a cushioning material 21 laminated on the resin sheet 4, a photosensor 15 including a light generating unit 5 and a light receiving unit 8 that are disposed to face each other so as to sandwich the resin sheet 4, and a processor 3 that detects a stress applied to the resin sheet 4 based on the light signal detected by the photosensor 15.

11 Claims, 6 Drawing Sheets

(51) Int. Cl.
  *A61B 5/00* (2006.01)
  *C08G 18/32* (2006.01)
  *G01L 1/24* (2006.01)
  *A61G 7/05* (2006.01)
  *A61B 5/11* (2006.01)
  *C08G 18/76* (2006.01)
  *C08J 5/18* (2006.01)
  *A47C 17/04* (2006.01)
  *A61G 7/015* (2006.01)

(52) U.S. Cl.
  CPC .......... *A61B 5/1117* (2013.01); *A61B 5/6892* (2013.01); *A61G 7/05* (2013.01); *C08G 18/3206* (2013.01); *C08G 18/7671* (2013.01); *C08J 5/18* (2013.01); *G01L 1/24* (2013.01); *G01L 1/241* (2013.01); *A47C 17/04* (2013.01); *A61B 5/1115* (2013.01); *A61B 5/447* (2013.01); *A61B 2562/0266* (2013.01); *A61G 7/015* (2013.01); *A61G 2203/30* (2013.01); *C08J 2375/04* (2013.01)

(58) Field of Classification Search
  CPC ..... A61B 5/6892; A61B 5/1115; A61B 5/447; A61B 2562/0266; A61G 7/015; A61G 2203/30; C08G 18/3206; C08G 18/7671; C08J 5/18; C08J 2375/04; G01L 1/24; G01L 1/241

See application file for complete search history.

(56) References Cited

U.S. PATENT DOCUMENTS

2012/0070112 A1   3/2012   Mitachi
  2013/0338330 A1   12/2013  Nakagawa

FOREIGN PATENT DOCUMENTS

WO      2014046054       3/2014
  WO      WO-2014046054 A1 *  3/2014   ........... A61B 5/6891

OTHER PUBLICATIONS

Extended European Search Report dated Aug. 13, 2018 for the corresponding European Patent Application No. 16746734.9.
  International Search Report dated Apr. 26, 2016 filed in PCT/JP2016/053563.

* cited by examiner

CUSHIONING MATERIAL HAVING SENSOR, AND BED

TECHNICAL FIELD

The present invention relates to a cushioning material having a sensor, and a bed. In particular, the present invention relates to a cushioning material having a sensor, and a bed having the cushioning material having a sensor.

BACKGROUND ART

In the field of medical caregiving, there may be a case where care receivers leave their bed on their own and fall or wander about. Also, for those care receivers who have difficulty in turning over on their own, bedsores may be caused. Therefore, there has been proposed a nursing bed having a pressure gauge therein to observe and manage weight shift (turning over, etc.) of the person on the bed and getting up.

To be specific, for example, Patent Document 1 below proposed a biological information detection device including a piezoelectric film that detects a pressure generated by a living body and outputs a pressure signal, a temperature detection means that detects the temperature of the environment in which the piezoelectric film is disposed and outputs a temperature signal according to the temperature, and an operational means that corrects the pressure signal according to the temperature signal and extracts biological information in accordance with the corrected pressure signal; and a bed device including the biological information detection device.

CITATION LIST

Patent Document

[Patent Document 1] Japanese Unexamined Patent Publication 2009-22567

SUMMARY OF THE INVENTION

Problem to be Solved by the Invention

However, because a piezoelectric film is used for pressure detection in the device described in Patent Document 1, there is a disadvantage that the correction with temperature is necessary. There is another disadvantage in that because piezoelectric films show piezoelectric effects many times, and therefore when used for nursing beds, changes in temperature from, for example, body temperature may be wrongly detected as a pressure.

Furthermore, because piezoelectric films generate electric signals in accordance with changes in pressure but do not generate electric signals under a constant pressure, and therefore for continuous monitoring of the pressure status using the piezoelectric film, a complicated process is necessary, for example, such as time integration of the signal intensity.

An object of the present invention is to provide a cushioning material having a sensor that does not necessitates correction with temperature, and allows for easy and precise pressure detection, and a bed including the cushioning material having a sensor.

Means for Solving the Problem

The present invention [1] includes a cushioning material having a sensor including a resin sheet composed of photoelastic resin, a cushioning material laminated on the resin sheet, a photosensor including a light generating unit and a light receiving unit that receives light generated from the light generating unit through the resin sheet, and a processor that detects a stress applied to the resin sheet based on a light signal detected by the photosensor.

The present invention [2] includes the cushioning material having a sensor of [1] above, wherein the light generating unit and the light receiving unit are disposed so as to overlap with the resin sheet on a plane of projection projected in a direction perpendicular to the thickness direction of the resin sheet.

The present invention [3] includes the cushioning material having a sensor of [1] or [2] above, wherein the light generating unit is disposed so as to overlap with the resin sheet on a plane of projection projected in a direction perpendicular to the thickness direction of the resin sheet, and the light receiving unit is disposed so as to overlap with the resin sheet on a plane of projection projected in the thickness direction of the resin sheet.

The present invention [4] includes the cushioning material having a sensor of [3] above, wherein the cushioning material includes a protruded accommodation unit for accommodating the light receiving unit.

The present invention [5] includes the cushioning material having a sensor of any one of [1] to [4] above, wherein the photoelastic resin has a photoelastic constant at 25° C. of $1000 \times 10^{-12}$ $Pa^{-1}$ or more and $100000 \times 10^{-12}$ $Pa^{-1}$ or less.

The present invention [6] includes the cushioning material having a sensor of any one of [1] to [5] above, wherein the photoelastic resin has a glass transition temperature of −60° C. or more and less than 25° C.

The present invention [7] includes the cushioning material having a sensor of any one of [1] to [6] above, wherein the photoelastic resin has a glass transition temperature of −60° C. or more and less than 0° C.

The present invention [8] includes the cushioning material having a sensor of any one of [1] to [7] above, wherein the photoelastic resin has a Young's modulus at 25° C. of 2 MPa or more and 5 MPa or less.

The present invention [9] includes the cushioning material having a sensor of any one of [1] to [8] above, wherein the photoelastic resin is polyurethane resin.

The present invention [10] includes the cushioning material having a sensor of any one of [1] to [9] above, wherein the photoelastic resin is produced from a polyurethane resin composition containing a polyisocyanate component and an active hydrogen group-containing component, the polyisocyanate component contains an aromatic ring-containing polyisocyanate having a 1,4-phenylene group (where a portion of the hydrogen atoms in the 1,4-phenylene group may be replaced with a methyl group and/or a methoxy group), and/or a 1,5-naphthylene group, and the active hydrogen group-containing component contains a high-molecular weight polyol having an average hydroxyl number of 20 to 500 mgKOH/g.

The present invention [11] includes the cushioning material having a sensor of [10] above, wherein the active hydrogen group-containing component further contains monol.

The present invention [12] includes a bed including the cushioning material having a sensor of any one of [1] to [11] above.

Effect of the Invention

In the cushioning material having a sensor and bed including the cushioning material having a sensor of the present invention, light generated from the light generating unit passes through the resin sheet composed of photoelastic resin at the stress-applied portion, and thereafter, is received by the light receiving unit, thus the processor detects the stress at the resin sheet.

Therefore, with the cushioning material having a sensor and bed including the cushioning material having a sensor of the present invention, the pressure can be detected easily and precisely without correction with temperature, and even under a constant pressure.

DESCRIPTION OF EMBODIMENTS

Figure 1:
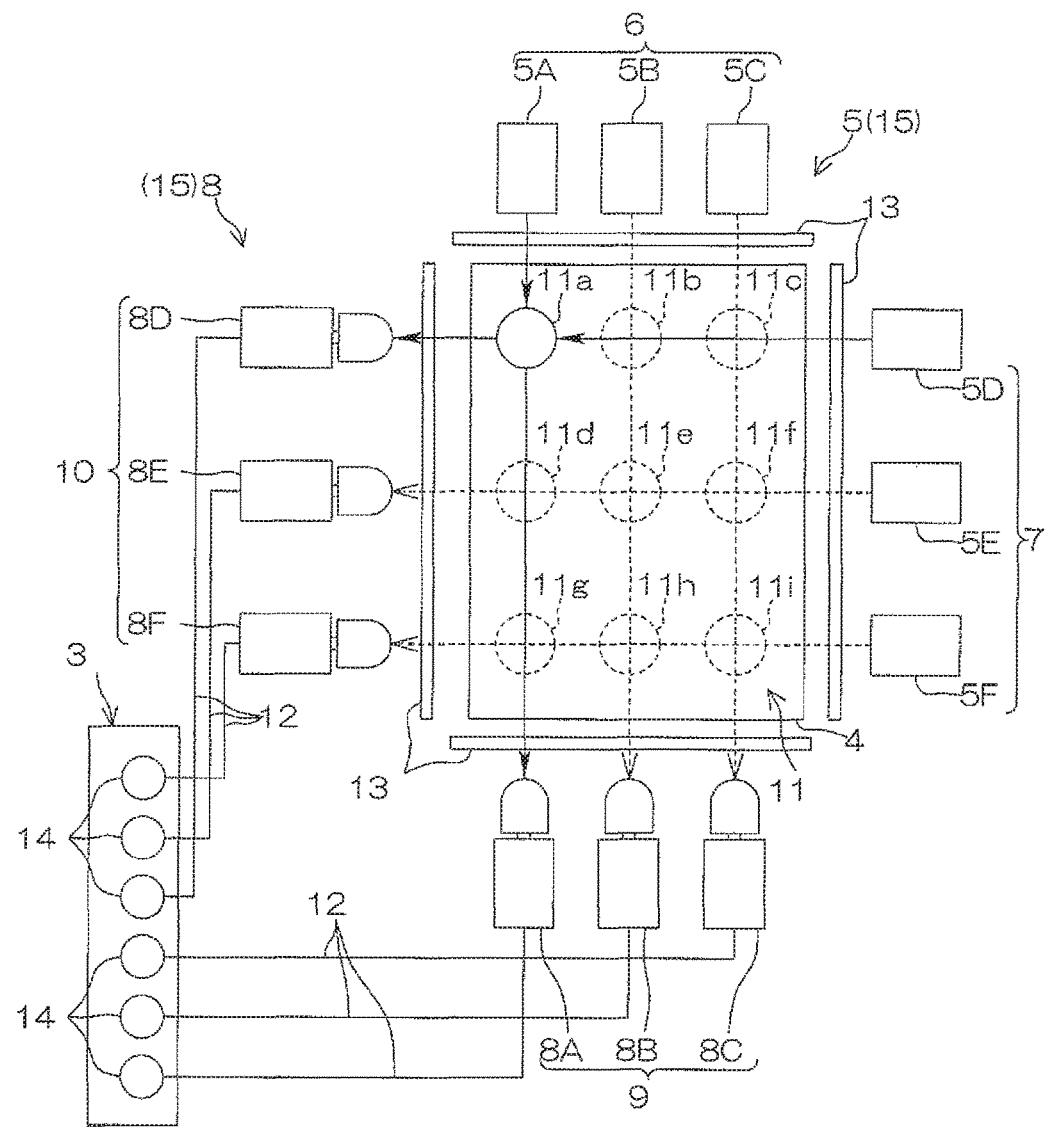
FIG. 1 shows a plan view of the cushioning material having a sensor in one embodiment of the present invention (embodiment in which the light generating unit and the light receiving unit are disposed outside the resin sheet).
Figure 2:
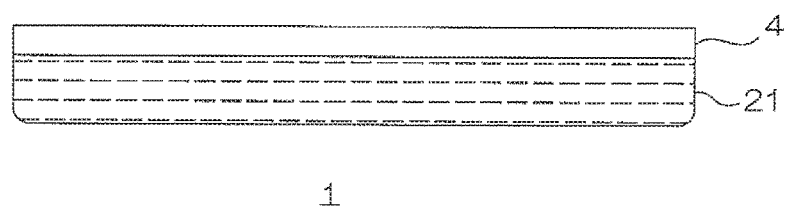
FIG. 2 shows a side view of the resin sheet and cushioning material of FIG. 1.

In FIG. 1 and FIG. 2, a cushioning material having a sensor 1 includes a resin sheet 4, a cushioning material 21, a photosensor 15, and a processor 3. In FIG. 1, the resin sheet 4 and the cushioning material 21 are overlapping with each other, and depiction of the cushioning material 21 is omitted. Therefore, separately, the side view of the resin sheet 4 and the cushioning material 21 are shown in FIG. 2. In FIG. 1, up-down direction on the plane of the paper is referred to as "longitudinal direction", and left-right direction on the plane of the paper is referred to as "lateral direction".

The resin sheet 4 is a molded article of photoelastic resin, and is formed into a sheet with a mold (casting mold) having a predetermined shape, or formed into a sheet with a predetermined shape by cutting after removed from the mold.

The photoelastic resin is not particularly limited as long as the photoelastic resin is resin showing photoelasticity. For example, polyurethane resin, vinyl chloride resin, and acrylic resin are used.

These photoelastic resin can be used singly, or can be used in combination of two or more.

In view of ease in production, preferably, polyurethane resin is used.

In the present invention, the polyurethane resin can be produced by allowing a polyurethane resin composition containing a polyisocyanate component and an active hydrogen group-containing component to react and cure.

The polyisocyanate component preferably include an aromatic ring-containing polyisocyanate, and examples of the aromatic ring-containing polyisocyanate include a 1,4-phenylene group (where a portion of the hydrogen atoms in the 1,4-phenylene group can be replaced with a methyl group and/or a methoxy group), and/or a 1,5-naphthylene group.

Examples of the aromatic ring-containing polyisocyanate containing a 1,4-phenylene group include benzene ring-containing polyisocyanates (to be specific, benzene ring-containing diisocyanates) such as 4,4'-diphenylmethane diisocyanate (4,4'-MDI), polymer of 4,4'-diphenylmethane diisocyanates (carbodiimide modified MDI, uretonimine modified MDI, acyl urea modified MDI, etc.), 2,4'-diphenylmethane diisocyanate (2,4'-MDI), 3,3'-dimethylbiphenyl-4,4'-diisocyanate (TODI), 3,3'-dimethoxybiphenyl-4,4'-diisocyanate, p-phenylenediisocyanate, 4,4'-diphenyl diisocyanate, 4,4'-diphenylether diisocyanate, 2,4-tolylene diisocyanate (2,4-TDI), and 1,4-xylylene diisocyanate (1,4-XDI).

Examples of the aromatic ring-containing polyisocyanate containing a 1,5-naphthylene group include naphthalene ring-containing polyisocyanate (to be specific, naphthalene ring-containing diisocyanate) such as 1,5-naphthalene diisocyanate (1,5-NDI).

Of the aromatic ring-containing polyisocyanate containing a 1,4-phenylene group and/or a 1,5-naphthylene group, preferably, 4,4'-diphenylmethane diisocyanate (4,4'-MDI), 3,3'-dimethylbiphenyl-4,4'-diisocyanate (TODI), and 1,5-naphthalene diisocyanate (1,5-NDI) are used.

The polyisocyanate component can be used singly, or can be used in combination of two or more.

The polyisocyanate component can contain other polyisocyanates as an optional component, in addition to the above-described aromatic ring-containing polyisocyanate as an essential component.

Examples of the other polyisocyanate include aromatic polyisocyanates (excluding the above-described aromatic ring-containing polyisocyanate), araliphatic polyisocyanates (excluding the above-described aromatic ring-containing polyisocyanate), alicyclic polyisocyanates, and aliphatic polyisocyanates.

Examples of the aromatic polyisocyanate include aromatic diisocyanates such as 2,2'-MDI, 2,6-TDI, m-phenylenediisocyanate, and 2,6-NDI.

Examples of the araliphatic polyisocyanates include araliphatic diisocyanates such as 1,3-xylylene diisocyanate (1,3-XDI), and tetramethylxylylene diisocyanate (TMXDI).

Examples of the alicyclic polyisocyanates include alicyclic diisocyanates such as 3-isocyanatomethyl-3,5,5-trimethylcyclohexyl isocyanate (isophorone diisocyanate, IPDI), 4,4'-,2,4'- or 2,2'-dicyclohexylmethanediisocyanate or a mixture thereof ($H_{12}$MDI), 1,3-bis(isocyanatomethyl) cyclohexane (hydrogenated xylylene diisocyanate, H6XDI), 2,5- or 2,6-bis(isocyanatomethyl) norbornane or a mixture thereof (NBDI), 1,3-cyclopentanediisocyanate, 1,4- or 1,3-cyclohexanediisocyanate or a mixture thereof, methyl-2,4-cyclohexanediisocyanate, and methyl-2,6-cyclohexanediisocyanate.

Examples of the aliphatic polyisocyanate include aliphatic diisocyanates such as trimethylenediisocyanate, tetramethylenediisocyanate (TMDI), pentamethylenediisocyanate (PDI), hexamethylenediisocyanate (HDI), 1,2-, 2,3- or 1,3-butylenediisocyanate, and 2,4,4- or 2,2,4-trimethyl-hexamethylenediisocyanate.

In the polyisocyanate component, the aromatic ring-containing polyisocyanate containing 1,4-phenylene group and/or 1,5-naphthylene group is blended in an amount of, relative to a total amount of the polyisocyanate component, for example, 30 mass % or more, more preferably 50 mass % or more, particularly preferably 90 mass % or more.

The polyisocyanate component has an aromatic ring concentration of, relative to the polyurethane resin composition, for example, 10 mass % or more, preferably 12 mass % or more, and generally for example, 30 mass % or less, preferably 26 mass % or less, more preferably 16 mass % or less.

When the polyisocyanate component has an aromatic ring concentration of the above-described lower limit or more, excellent photoelasticity can be obtained.

When the polyisocyanate component has an aromatic ring concentration of the above-described upper limit or less, excellent photoelasticity can be obtained.

The aromatic ring concentration of the polyisocyanate component is the mass ratio of the aromatic ring derived from the polyisocyanate component in the polyurethane resin composition, and does not include the aromatic ring derived from the cyano compound to be described later.

The aromatic ring concentration is calculated, when the polyisocyanate component contains 1,4-phenylene group, by setting the molecular weight of the polyisocyanate to 78 (g/mol), and when the polyisocyanate component contains 1,5-naphthylene group, by setting the molecular weight of the polyisocyanate to 128 (g/mol).

The active hydrogen group-containing component is a compound having an active hydrogen group (for example, hydroxyl group, amino group, etc.), and for example, polyol and polyamine, preferably polyol is used.

The polyol preferably contains a high-molecular weight polyol.

The high-molecular weight polyol is a compound having two or more hydroxyl groups and an average hydroxyl number (described later) of 20 to 500 mgKOH/g, and when the average functionality (described later) is 2, it is a compound having a number average molecular weight of 225 or more, or when the average functionality is 3, it is a compound having a number average molecular weight of 337 or more.

Examples of the high-molecular weight polyol include polyetherpolyol, polyesterpolyol, polycarbonatepolyol, polyolefinpolyol, dimer polyol, polyurethane polyol, polyoxyalkylenepolyester block copolymer polyol, acrylic polyol, epoxypolyol, natural oil polyol, silicone polyol, and fluorine polyol.

Examples of the polyether polyol include polyoxyalkylene polyol such as polyalkylene (C2 to 3) polyol and polytetramethylene ether polyol.

Examples of the polyalkylene (C2 to 3) polyol include addition polymerized product (random and/or block copolymer of two or more alkylene oxides) of alkylene oxides such as, for example, ethylene oxide and propylene oxide using the low-molecular-weight polyol as an initiator. To be specific, for example, polyethylene glycol, polypropylene glycol, and an ethylene oxide-propylene oxide copolymer (random and/or block copolymer) are used.

The low-molecular-weight polyol is a compound having two or more hydroxyl groups and an average hydroxyl number (described later) of more than 500 mgKOH/g, and when it has a functionality (described later) of 2, it is diol having a molecular weight of 40 or more and less than 225, or when it has a functionality of 3, it is triol having a molecular weight of 40 or more and less than 337.

Examples of the low-molecular-weight polyol include diols (dihydric alcohol) such as aliphatic diols (having 2 to 13 carbon atoms) including ethylene glycol, propylene glycol (1,2-propanediol), trimethyleneglycol (1,3-propanediol), 1,4-butyleneglycol (1,4-butanediol), 1,3-butyleneglycol (1,3-butanediol), 1,2-butyleneglycol, 2-methyl-1,3-propanediol, 1,5-pentanediol, neopentyl glycol, 3-methyl-1,5-pentanediol, 2,4-diethyl-1,5-pentanediol, 1,6-hexanediol, and 2-ethyl-1,3-hexanediol, alkane (having 7 to 13 carbon atoms) diols, and alkene (having 4 to 13 carbon atoms) diols such as 1,4-dihydroxy-2-butene and 2,6-dimethyl-1-octene-3,8-diol; alicyclic diols (having 6 to 13 carbon atoms) such as cyclohexanedimethanol; aromatic diols (aromatic ring-containing diol containing an aromatic ring and having 6 to 13 carbon atoms) such as bishydroxyethoxybenzene and xylene glycol; and diols (having 2 to 9 carbon atoms) of oxyalkylene alcohols including diethylene glycol, trioxyethylene glycol, tetraoxyethylene glycol, dipropylene glycol, and trioxypropylene glycol; triols (trihydric alcohol) such as aliphatic triols having 3 to 6 carbon atoms including glycerin, 2-methyl-2-hydroxvmethyl-1,3-propanediol, 2,4-dihydroxy-3-hvdroxymethylpentane, 1,2,6-hexanetriol, trimethylolpropane, and 2,2-bis(hydroxymethyl)-3-butanol, and other aliphatic triols (having 7 to 20 carbon atoms); tetraols (tetrahydric alcohol)(having 5 to 27 carbon atoms) such as tetramethylolmethane (pentaerythritol) and diglycerin (diglycerol); pentaols (pentahydric alcohol) (having 5 to 33 carbon atoms) such as xylitol; hexaols (hexahydric alcohol) (having 6 to 40 carbon atoms) such as sorbitol, mannitol, allitol, iditol, dulcitol, altritol, inositol, and dipentaerythritol; heptahydric alcohols (heptaol) (having 7 to 47 carbon atoms) such as perseitol; and octaol (octahydric alcohol) (having 8 to 54 carbon atoms) such as sucrose.

These low-molecular-weight polyols can be used singly, or can be used in combination of two or more.

Examples of the polytetramethylene ether polyol include a ring-opening polymerized product produced by cationic polymerization of tetrahydrofuran; noncrystalline polytetramethylene ether glycol produced by copolymerizing the above-described diol with a polymerization unit of tetrahydrofuran; and noncrystalline polytetramethylene ether glycol produced by copolymerizing ethylene oxide, propylene-oxide, epichlorohydrin and/or benzylglycidyl ether with a polymerization unit of tetrahydrofuran.

Examples of the polyetherpolyol include aromatic ring-containing polyol produced by addition polymerization of aromatic diols such as the above-described aromatic ring-containing diol (to be specific, bishydroxyethoxybenzene, etc.) having 6 to 13 carbon atoms, and aromatic ring-containing diol (to be specific, bishydroxyethylterephthalate, bisphenol A, etc.) having a hydroxyl number of 500 mgKOH/g or less with ethylene oxide, propylene oxide, and/or tetrahydrofuran.

For the polyetherpolyol, preferably, polytetramethylene ether glycol is used.

For the polyesterpolyol, for example, polyesterpolyol produced by the reaction of the above-described low-molecular-weight polyol with polybasic acid or its acid anhydride or its acid halide is used.

Examples of the polybasic acid and its acid anhydride or its acid halide include carboxylic acid (dicarboxylic acid) such as oxalic acid, malonic acid, succinic acid, methyl succinic acid, glutaric acid, adipic acid, 1,1-dimethyl-1,3-dicarboxypropane, 3-methyl-3-ethyl glutaric acid, azelaic acid, sebacic acid, other aliphatic dicarboxylic acids (C11-C13), hydrogenated dimer acid, maleic acid, fumaric acid, itaconic acid, orthophthalic acid, isophthalic acid, terephthalic acid, toluene dicarboxylic acid, dimer acid and HET acid; and acid anhydride derived from these carboxylic acids, such as oxalic anhydride, succinic anhydride, maleic anhydride, phthalic anhydride, 2-alkyl (C12-C18) succinic anhydride, tetrahydrophtalic anhydride and trimellitic anhydride; and also acid halide derived from these carboxylic acid anhydrides such as oxalic dichloride, adipic dichloride and sebacic dichloride.

Examples of the polyesterpolyol include lactone-based polyester polyol such as polycaprolactone polyol and polyvalerolactone polyol produced by ring-opening polymerization of lactones such as ε-caprolactone and γ-valerolactone using the above-described low-molecular-weight polyol as an initiator.

Examples of the polyester polyol further include vegetable oil polyesterpolyol produced by condensation reaction of the above-described low-molecular-weight polyol with hydroxycarboxylic acid such as hydroxyl group-containing vegetable oil fatty acid (for example, castor oil fatty acid containing ricinoleic acid and hydrogenated castor oil fatty acid containing 12-hydroxystearic acid, etc.) under known conditions.

The polycarbonate polyol can be produced by, for example, allowing phosgene, dialkylcarbonate, diallylcarbonate, and alkylenecarbonate to react in the presence or absence of a catalyst, using the above-described low-molecular-weight polyol as an initiator. For the polycarbonatepolyol, preferably, polycarbonatediol using diol as an initiator is used.

For the polyolefinpolyol, polybutadienepolyol and polyisoprenediol produced by adding a hydroxyl group to a terminal of polymer of conjugated double bond-containing monomer such as butadiene and isoprene are used.

Examples of the dimer polyol include dimer diols produced by reducing unsaturated fatty acid dimer having 18 carbon atoms as a main component, which can be generally obtained as an industrial material.

Examples of the polyurethane polyol include polyetherpolyurethane polyol, polyesterpolyurethane polyol, polycarbonatepolyurethane polyol, or polyesterpolyetherpolyurethane polyol produced by allowing the polyetherpolyol, polyesterpolyol and/or polycarbonatepolyol as described above to react with the above-described polyisocyanate component at a ratio such that the equivalent ratio (OH/NCO) of the hydroxyl group relative to the isocyanate group is more than 1.

Examples of the polyoxyalkylenepolyester block copolymer polyol include, as shown in Japanese Examined Patent Publication Sho 48-10078, those having a structure in which polyoxyalkylene polyol is blocked with polyester chain. That is, examples include those polyoxyalkylene polyol or its derivative having a hydroxyl group in which the portion replaced with the hydrogen atom in the hydroxy group is represented by general formula (A) below:

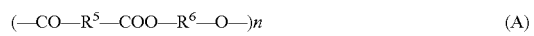

$$(-CO-R^5-COO-R^6-O-)_n \qquad (A)$$

(where R5 and R6 each represents a divalent hydrocarbon group, and n represents a number more than 1 in average).

In general formula (A), examples of the divalent hydrocarbon group represented by R5 include saturated aliphatic or aromatic polycarboxylic acid residue, examples of the divalent hydrocarbon group represented by R6 include a residue produced by cleaving a compound having a cyclic ether group, and n is preferably an integer of 1 to 20.

The polyoxyalkylenepolyester block copolymer polyol is produced by allowing the above-described polyoxyalkylene polyol (polyetherpolyol) to react with polycarboxylic acid anhydride and alkyleneoxide.

The high-molecular weight polyol has an average hydroxyl number of 20 to 500 mgKOH/g, preferably 80 to 300 mgKOH/g, more preferably 100 to 250 mgKOH/g.

The hydroxyl number (unit: mgKOH/g) of the high-molecular weight polyol can be determined by acetylation or phthalation accordance to method A or method B of JIS K 1557-1.

The average hydroxyl number (unit: mgKOH/g) of the high-molecular weight polyol is the same as the hydroxyl number of the high-molecular weight polyol when the high-molecular weight polyol is used singly. Meanwhile, the average hydroxyl number of the high-molecular weight polyol is their average value when the high-molecular weight polyol is used in combination.

When the average hydroxyl number of the high-molecular weight polyol is more than the range described above, the polyurethane resin (molded article, resin sheet) may have an excessively high Young's modulus, and the desired photoelastic constant may not be obtained. Meanwhile, when the average hydroxyl number is less than the range described above, the glass transition temperature is excessively low, and processability and scratch resistance may be reduced.

The high-molecular weight polyol has an average functionality of, for example, 1.9 to 3, preferably 1.9 to 2.5, more preferably 2.0 to 2.2.

The functionality of the high-molecular weight polyol is a number of the hydroxyl group of the high-molecular weight polyol. To be specific, it is the number of active hydroxyl groups per one molecule.

The average functionality of the high-molecular weight polyol is an average value of the active hydroxyl group per one molecule of the high-molecular weight polyol. That is, when high-molecular weight polyols having different functionalities are mixed (used in combination), the numeral value showing the ratio of the number of the active hydroxyl group of the mixture relative to the number of the molecules of the mixture of the high-molecular weight polyol is the average functionality of the high-molecular weight polyol.

The average functionality of the high-molecular weight polyol can also be determined from formula (B) below:

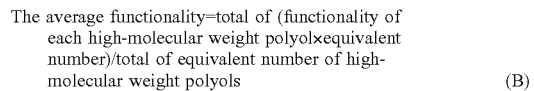

The average functionality=total of (functionality of each high-molecular weight polyol×equivalent number)/total of equivalent number of high-molecular weight polyols        (B)

The high-molecular weight polyol has a number average molecular weight of, for example, 225 to 20,000, preferably 500 to 15,000.

The number average molecular weight can be determined from formula (C) below:

The number average molecular weight=56100×average functionality/average hydroxyl number (C)

When the average functionality of the high-molecular weight polyol is more than the above-described range, the polyurethane resin (molded article, resin sheet) may not achieve a desired photoelastic constant. Meanwhile, when the average functionality is less than the above-described range, the Young's modulus may be excessively low, and processability and scratch resistance may be reduced.

For the high-molecular weight polyol, preferably, polyetherpolyol, polyesterpolyol, polycarbonatepolyol, and polyolefinpolyol are used.

More preferably, polytetramethylene ether polyol, and polycarbonatepolyol (to be specific, polycarbonatediol) are used.

The polytetramethylene ether glycol has an average hydroxyl number of 100 to 250 mgKOH/g, preferably 100 to 220 mgKOH/g. When the polytetramethylene ether glycol has an average hydroxyl number within the above-described range, a high photoelasticity and high rigidity can be achieved both.

The polycarbonate diol has an average hydroxyl number of 100 to 250 mgKOH/g, preferably 150 to 250 mgKOH/g. When the polycarbonate diol has an average hydroxyl number within the above-described range, high photoelasticity and high rigidity can be achieved both.

These high-molecular weight polyols can be used singly, or can be used in combination of two or more.

The polyol can contain the above-described low-molecular-weight polyol, in addition to the above-described high-molecular weight polyol.

When the polyol contains the low-molecular-weight polyol, the average hydroxyl number of the polyol increases, and to the extent of the increase, to adjust the isocyanate index (described later) to a desired value, a large amount of the above-described polyisocyanate component (preferably, aromatic ring-containing polyisocyanate) can be blended in the polyurethane resin composition. Therefore, the photoelastic constant of the polyurethane resin (molded article, resin sheet) can be increased.

For the low-molecular-weight polyol, preferably diol, triol, and tetraol are used. To be specific, diol having 2 to 10 carbon atoms, triol having 3 to 10 carbon atoms, and tetraol having 5 to 10 carbon atoms are used.

Examples of the diol having 2 to 10 carbon atoms include aliphatic diols (having 2 to 10 carbon atoms) including ethylene glycol, propylene glycol, trimethyleneglycol (1,3-propanediol), 1,4-butyleneglycol, 1,3-butyleneglycol, 1,2-butyleneglycol, 2-methyl-1,3-propanediol, 1,5-pentanediol, neopentyl glycol, 3-methyl-1,5-pentanediol, 2,4-diethyl-1,5-pentanediol, 1,6-hexanediol, 2-ethyl-1,3-hexanediol, and alkane (having 7 to 10 carbon atoms) diols; alkene (having 4 to 10 carbon atoms) diols including 1,4-dihydroxy-2-butene, and 2,6-dimethyl-1-octene-3,8-diol; alicyclic diols (having 6 to 10 carbon atoms) such as cyclohexanedimethanol; aromatic diols (aromatic ring-containing diol having 6 to 10 carbon atoms) such as xylene glycol; and diols (having 2 to 10 carbon atoms) of oxyalkylene alcohol including diethylene glycol, trioxyethylene glycol, tetraoxyethylene glycol, dipropylene glycol, and trioxypropylene glycol.

Examples of the triol having 3 to 10 carbon atoms include triols such as aliphatic triol having 3 to 6 carbon atoms including glycerin, 2-methyl-2-hydroxymethyl-1,3-propanediol, 2,4-dihydroxy-3-hydroxymethylpentane, 1,2,6-hexanetriol, trimethylolpropane, and 2,2-bis(hydroxymethyl)-3-butanol, and other aliphatic triols (having 7 to 10 carbon atoms).

Examples of the tetraol having 5 to 10 carbon atoms include tetraols such as tetramethylolmethane, and diglycerin.

Examples of the low-molecular-weight polyol also include polyalkylene oxide having a number average molecular weight of 400 or less. Examples of such polyalkylene oxide include polyethylene glycol (polyoxyethyleneetherglycol), polypropylene glycol (polyoxypropyleneetherglycol), and polyethylene polypropylene glycol (random or block copolymer) produced by addition reaction of alkylene oxide such as ethylene oxide and/or propylene oxide using the above-described low-molecular-weight polyol (diol, triol, etc.) as an initiator.

The low-molecular-weight polyol can be used singly, or can be used in combination of two or more.

Preferably, triol is at least used, and to be specific, triol having 3 to 10 carbon atoms is used singly, or triol having 3 to 10 carbon atoms and diol having 2 to 10 carbon atoms are used in combination.

The low-molecular-weight polyol is blended in an amount of, relative to 100 parts by mass of the high-molecular weight polyol, for example, 0.1 to 30 parts by mass, preferably 0.5 to 25 parts by mass.

When the triol having 3 to 10 carbon atoms is used singly, for example, 10 parts by mass or less, preferably 9 parts by mass or less, more preferably 0.5 to 6 parts by mass of the triol having 3 to 10 carbon atoms is blended relative to 100 parts by mass of the high-molecular weight polyol.

When the triol having 3 to 10 carbon atoms is blended in more than the above-described range, the polyurethane resin (molded article, resin sheet) becomes non-transparent, light may not pass the polyurethane resin (molded article, resin sheet), and the Young's modulus of the polyurethane resin (molded article, resin sheet) may become excessively high.

When the triol having 3 to 10 carbon atoms and the diol having 2 to 10 carbon atoms are used in combination, the triol having 3 to 10 carbon atoms is blended in an amount of, relative to 100 parts by mass of the high-molecular weight polyol, for example, 0.5 to 10 parts by mass, preferably 0.6 to 6 parts by mass, and the diol having 2 to 10 carbon atoms is blended in an amount of, relative to 100 parts by mass of the high-molecular weight polyol, for example, 25 parts by mass or less, preferably 0.1 to 10 parts by mass. When the triol having 3 to 10 carbon atoms and the diol having 2 to 10 carbon atoms are blended within the above-described range, high photoelasticity and high rigidity can be achieved both.

When the triol having 3 to 10 carbon atoms and the diol having 2 to 10 carbon atoms are used in combination, they are blended in total of, relative to 100 parts by mass of the high-molecular weight polyol, for example, 0.1 to 30 parts by mass, preferably 0.5 to 25 parts by mass, more preferably 0.7 to 6 parts by mass.

When the total amount of the triol and the diol is less than the above-described range, the Young's modulus may be excessively reduced, moldability and scratch resistance may be reduced, and the photoelastic constant may be reduced. When the total amount of the triol and the diol is more than the above-described range, the Young's modulus may be excessively high.

The active hydrogen group-containing component may further contain monol, in view of improving sleeping comfort in bed (described later).

The monol is a compound (monohydric alcohol) having one hydroxyl group, and examples thereof include methanol, ethanol, propanol, isopropanol, butanol, isobutanol, s-butanol, t-butanol, pentanol, hexanol, 2-ethyl-1-hexanol, heptanol, octanol, nonanol, decanol, undecanol, dodecanol, tridecanol, tetradecanol, hexadecanol (1-hexadecanol, etc.), heptadecanol, octadecanol (1-octadecanol, etc.), nonadecanol, eicosanol (1-eicosanol, etc.), tetracosanol (1-tetracosanol, etc.), and their isomers, and furthermore, other alkanol (C20 to 50 alcohol); alkenyl alcohols such as oleyl alcohol and linolyl alcohol; alkadienols such as octadienol; and aliphatic monols such as polyethylenebutylenemonol. Examples of the monoalcohol include alicyclic monols such as cyclohexanol and methylcyclohexanol, and araliphatic monols such as benzvlalcohol.

These monols may be used singly or in combination of two or more.

For the monol, preferably aliphatic monol is used, more preferably, 2-ethyl-1-hexanol is used.

When the monol is blended, the monol is blended in an amount of, relative to 100 parts by mass of the high-molecular weight polyol, for example, 0.1 or more, preferably 0.2 or more, and for example, 1.0 or less, preferably 0.5 or less.

The active hydrogen group-containing component is blended so that the high-molecular weight polyol in the active hydrogen group-containing component relative to 100 parts by mass of the polyisocyanate component is, for example, 120 to 400 parts by mass, preferably 125 to 333 parts by mass.

In other words, the polyisocyanate component content relative to 100 parts by mass of the high-molecular weight polyol is, for example, 25 to 85 parts by mass, preferably 30 to 80 parts by mass. When the polyisocyanate component content is within the above-described range, high rigidity can be achieved.

When the polyisocyanate component content is more than the above-described range, the Young's modulus is excessively high, and the desired photoelastic constant may not be achieved in polyurethane resin (molded article, resin sheet).

When the polyisocyanate component content is less than the above-described range, the desired photoelastic constant may not be achieved in the polyurethane resin (molded article, resin sheet).

The polyurethane resin composition of the present invention can contain a plasticizer.

The plasticizer is blended in the polyurethane resin composition as necessary to reduce the glass transition temperature of the polyurethane resin (molded article, resin sheet), and examples thereof include a cyano compound, phthalic acid ester (for example, phthalic acid di-2-ethylhexyl, dioctyl phthalate), adipic acid ester (for example, adipic acid dioctyl), sebacic acid ester (for example, sebacic acid dioctyl), phosphoric acid triglycidyl, acetylcitric acid tributyl, epoxidized soybean oil, trimellitic acidtrioctyl, alkylbenzene, alkylbiphenyl (for example, 4-pentylbiphenyl), chlorinated paraffin, a high boiling point solvent, ion liquid (for example, 1-ethyl-2,3-dimethylimidazolium bis(trifluoromethanesulfonyl) imide), and a polyester plasticizer. Preferably, a cyano compound is used.

When the cyano compound is blended in the polyurethane resin composition, the Young's modulus of the molded article can be reduced, and with the reduced Young's modulus, processability of the polyurethane resin (molded article, resin sheet) can be improved, and the photoelastic constant can also be increased.

The cyano compound has, for example, 14 to 24 carbon atoms, and a 4-cyanophenyl group (where a portion of hydrogen atoms in 4-cyanophenyl group may be replaced with fluorine atoms).

When the cyano compound has the 4-cyanophenyl group, the photoelastic constant can be increased even more.

In the 4-cyanophenyl group, for example, the hydrogen atoms at positions 2 to 6 are replaced with the fluorine atoms, preferably, the hydrogen atom at position 2 is replaced with the fluorine atom.

Examples of the cyano compound include, to be specific, a biphenyl compound represented by formula (1) below:

[Chemical Formula 1]

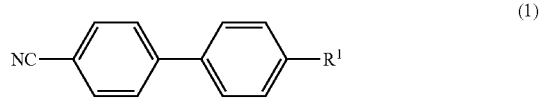

(1)

(where R1 is an alkyl group having 1 to 11 carbon atoms, a 4-alkylphenyl group having 7 to 11 carbon atoms, or a 4-alkylcyclohexyl group having 7 to 11 carbon atoms), an ether compound represented by formula (2) below,

[Chemical Formula 2]

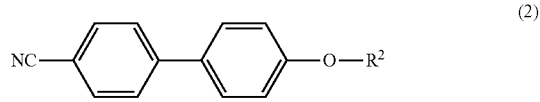

(2)

(where R2 represents an alkyl group having 1 to 11 carbon atoms), a cyclohexyl compound represented by formula (3) below,

[Chemical Formula 3]

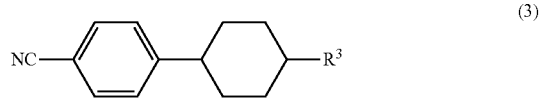

(3)

(R3 represents an alkyl group having 1 to 11 carbon atoms, or an alkenyl group having 5 to 11 carbon atoms), and a phenyl ester compound represented by formula (4) below,

[Chemical Formula 4]

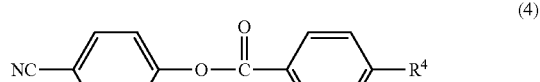

(4)

(R4 represents a hydrogen atom or an alkyl group having 1 to 10 carbon atoms).

In the above-described formula (1), examples of the alkyl group having 1 to 11 carbon atoms represented by R1 include a straight chain or branched alkyl group such as methyl, ethyl, propyl, isopropyl, butyl, isobutyl, tert-butyl, pentyl, isopentyl, tert-pentyl, hexyl, heptyl, octyl, nonyl, isononyl, decyl, and dodecyl. Preferably, an alkyl group having 2 to 7 carbon atoms is used.

In the above-described formula (1), examples of the 4-alkylphenyl group having 7 to 11 carbon atoms represented by R1 include a 4-alkylphenyl group having a straight chain or branched alkyl moiety with 1 to 5 carbon atoms such as 4-methylphenyl, 4-ethylphenyl, 4-propylphenyl, 4-isopropylphenyl, 4-pentylphenyl, 4-isopentylphenyl, and 4-tertpentylphenyl. Preferably, a 4-alkylphenyl group having 9 to 11 carbon atoms with an alkyl moiety with 3 to 5 carbon atoms is used.

Examples of the 4-alkylcyclohexyl group having 7 to 11 carbon atoms include a 4-alkylcyclohexyl group having a straight chain or branched alkyl moiety with 1 to 5 carbon atoms such as 4-methylcyclohexyl, 4-ethylcyclohexyl, 4-propylcyclohexyl, 4-isopropylcyclohexyl, 4-pentylcyclohexyl, 4-isopentylcyclohexyl, and 4-tertpentylcyclohexyl. Preferably, a 4-alkylcyclohexyl group having 9 to 11 carbon atoms with an alkyl moiety having 3 to 5 carbon atoms is used.

For R1 represented by the above-described formula (1), preferably an alkyl group having 1 to 11 carbon atoms, and a 4-alkylcyclohexyl group having 7 to 11 carbon atoms are used.

For the biphenyl compound represented by the above-described formula (1), to be specific, 4-cyano-4'-methylbiphenyl, 4-cyano-4'-pentylbiphenyl, and 4-cyano-4'-(4-pentylcyclohexyl) biphenyl are used.

In the above-described formula (2), examples of the alkyl group having 1 to 11 carbon atoms represented by R2 include the alkyl groups given as examples of the alkyl group having 1 to 11 carbon atoms represented by R1 in the above-described formula (1).

Examples of the ether compound represented by the above-described formula (2) include, to be specific, 4-cyano-4'-pentyloxybiphenyl.

In the above-described formula (3), examples of the alkyl group having 1 to 11 carbon atoms represented by R3 include the alkyl groups given as examples of the alkyl group having 1 to 11 carbon atoms represented by R1 in the above-described formula (1).

In the above-described formula (3), examples of the alkenyl group having 5 to 11 carbon atoms represented by R3 include pentenyl, hexenyl, heptenyl, octenyl, nonenyl, decynyl, and dodecenyl.

In the above-described formula (3), for R3, preferably, an alkyl group having 1 to 11 carbon atoms is used.

Examples of the cyclohexyl compound represented by the above-described formula (3) include, to be specific, 4-(4-pentylcyclohexyl) benzonitrile, 4-((3-pentenyl)-4-cyclohexyl) benzonitrile, and 2-fluoro-4-(4-pentylcyclohexyl) benzonitrile.

In the above-described formula (4), examples of the alkyl group having 1 to 10 carbon atoms represented by R4 include, of the alkyl groups given as examples of the alkyl group having 1 to 11 carbon atoms represented by R1 in the above-described formula (1), the alkyl groups of the alkyl group having 1 to 10 carbon atoms are used.

Examples of the phenylester compound represented by the above-described formula (4) include 4-propylbenzoic acid 4-cyanophenyl, 4-heptylbenzoic acid 4-cyanophenyl, and 4-pentylbenzoic acid 4-cyano-3,5-difluorophenyl.

Examples of the cyano compound also include cyanobenzene and 4-methoxybenzene.

The cyano compound can be used singly, or can be used in combination of two or more.

Of the cyano compound, preferably, a biphenyl compound is used.

The plasticizer is blended in an amount of, relative to 100 parts by mass of the high-molecular weight polyol, for example, 100 parts by mass or less, preferably 1 to 60 parts by mass, more preferably 5 to 30 parts by mass.

When the plasticizer is blended in more than the above-described range, the Young's modulus of the polyurethane resin (molded article, resin sheet) may be excessively reduced, and appearance of the polyurethane resin (molded article, resin sheet) may be non-transparent.

By formulating (blending) the above-described polyisocyanate component and the active hydrogen group-containing component, and as necessary the plasticizer, a polyurethane resin composition is produced.

A preferable combination of the components blended in the polyurethane resin composition include, for example, an aromatic ring-containing polyisocyanate containing a 1,4-phenylene group, polyetherpolyol, diol having 2 to 10 carbon atoms, and triol having 3 to 10 carbon atoms. To be specific, the combination can be benzene ring-containing diisocyanate, polytetramethylene ether polyol, aliphatic diol having 2 to 10 carbon atoms, and aliphatic triol having 3 to 6 carbon atoms.

A preferable combination of the components formulated in the polyurethane resin composition also include, for example, various types of aromatic ring-containing polyisocyanates, polyetherpolyol, diol having 2 to 10 carbon atoms, and triol having 3 to 10 carbon atoms. To be specific, the combination can be a combination of benzene ring-containing diisocyanate and naphthalene ring-containing diisocyanate, polytetramethylene ether polyol, aliphatic diol having 2 to 10 carbon atoms, and aliphatic triol having 3 to 6 carbon atoms, or a combination of two different benzene ring-containing diisocyanates, polytetramethylene ether polyol, aliphatic diol having 2 to 10 carbon atoms, and aliphatic triol having 3 to 6 carbon atoms.

A preferable combination of the components formulated in the polyurethane resin composition also include, for example, aromatic ring-containing polyisocyanate containing a 1,4-phenylene group, polyetherpolyol, diol having 2 to 10 carbon atoms, triol having 3 to 10 carbon atoms, and a plasticizer. To be specific, the combination can be benzene ring-containing diisocyanate, polytetramethylene ether polyol, aliphatic diol having 2 to 10 carbon atoms, aliphatic triol having 3 to 6 carbon atoms, and a biphenyl compound.

A preferable combination of the components formulated in the polyurethane resin composition also include, for example, aromatic ring-containing polyisocyanate containing a 1,4-phenylene group, polycarbonatepolyol, triol having 3 to 10 carbon atoms, and a plasticizer. To be specific, the combination can be benzene ring-containing diisocyanate, polycarbonatediol, aliphatic triol having 3 to 6 carbon atoms, and a biphenyl compound.

A preferable combination of the components formulated in the polyurethane resin composition also include, for example, a plurality of types of the aromatic ring-containing polyisocyanate containing a 1,4-phenylene group, polyetherpolyol, diol having 2 to 10 carbon atoms, triol having 3 to 10 carbon atoms, and a plasticizer. To be specific, the combination can be two different types of benzene ring-containing diisocyanates, polytetramethylene ether polyol, aliphatic diol having 2 to 10 carbon atoms, aliphatic triol having 3 to 6 carbon atoms, and a biphenyl compound or an ether compound.

A preferable combination of the components formulated in the polyurethane resin composition also include, for example, various types of aromatic ring-containing polyisocyanates, polycarbonatepolyol, and triol having 3 to 10 carbon atoms. To be specific, the combination can be benzene ring-containing diisocyanate and naphthalene ring-containing diisocyanate, polycarbonatediol, and aliphatic triol having 3 to 10 carbon atoms.

A preferable combination of the components formulated in the polyurethane resin composition also include, for example, aromatic ring-containing polyisocyanate containing a 1,4-phenylene group, polyesterpolyol, and triol having 3 to 10 carbon atoms. To be specific, the combination can be benzene ring-containing polyisocyanate, polyesterdiol of polycondensate of dicarboxylic acid and diol, and aliphatic triol having 3 to 10 carbon atoms.

The polyurethane resin (molded article, resin sheet) can be produced by allowing polyisocyanate and polyol to react with each other from the polyurethane resin composition, and curing and molding the polyurethane resin composition.

The reaction of the polyisocyanate component and the active hydrogen group-containing component can be performed in accordance with, for example, a known molding method such as one shot process and prepolymer process.

In the one shot process, for example, the polyisocyanate component and the active hydrogen group-containing component are formulated (mixed) so that the isocyanate index (ratio of the isocyanate group concentration relative to the hydroxyl group concentration multiplied by 100, NCO concentration hydroxyl group concentration×100) is, for example, 70 to 400, preferably 80 to 150, and then the mixture is injected into a mold, and curing reaction is conducted at, for example, 0° C. to 250° C., preferably room temperature (20° C.) to 150° C., for, for example, 1 minute to 7 days, preferably for 10 minutes to 2 days.

In the curing reaction, a urethanizing catalyst can be added. Examples of the urethanizing catalyst include a tin catalyst (for example, tin octylate, etc.), lead catalyst (for example, lead octylate, etc.), bismuth catalyst, titanium catalyst, zirconium catalyst, organic metal catalyst, and amine catalyst, and preferably, in view of achieving a high photoelastic constant, a lead catalyst is used.

The urethanizing catalyst is blended in an amount of, relative to 100 parts by mass of the polyisocyanate component, for example, 0.0001 to 2.0 parts by mass, preferably 0.0005 to 1.0 parts by mass.

The above-described curing reaction can also be conducted in the presence of a known solvent.

The polyurethane resin (molded article, resin sheet) molded into a predetermined shape can be produced by, after injecting into the mold and subjecting it to curing reaction, removing from the mold.

Alternatively, polyurethane resin (molded article, resin sheet) having a predetermined thickness can be formed by applying the polyurethane resin composition on a substrate such as, for example, a glass substrate, and a resin film with a uniform thickness to form a film, and then curing.

The polyurethane resin (molded article, resin sheet) can be released from the substrate after curing. Alternatively, the polyurethane resin (molded article, resin sheet) can be used while it is attached to the substrate without releasing it from the substrate.

In the prepolymer, for example, first, the polyisocyanate component is allowed to react with a portion of the active hydrogen group-containing component (for example, high-molecular weight polyol), to synthesize an isocyanate group-terminated prepolymer having an isocyanate group at its molecular terminal. Then, the produced isocyanate group-terminated prepolymer is allowed to react with the remaining portion of the active hydrogen group-containing component (chain extender; for example, low-molecular-weight polyol (and as necessary high-molecular weight polyol, monol))(chain extension), and subjected to curing reaction.

The isocyanate group-terminated prepolymer is synthesized in the following manner. The polyisocyanate component and a portion of the active hydrogen group-containing component is formulated (mixed) such that the isocyanate index (NCO concentration/hydroxyl group concentration× 100) is, for example, 110 to 2,000, preferably 150 to 1,000, and the mixture is allowed to react in a reaction vessel at, for example, room temperature to 150° C., preferably 40 to 120° C., for, for example, 0.5 to 18 hours, preferably 2 to 10 hours.

The above-described isocyanate group-terminated prepolymer can be synthesized in the presence of a known solvent.

After synthesis of the above-described isocyanate group-terminated prepolymer, the unreacted polyisocyanate component can be removed by the removal methods including, for example, distillation such as thin film distillation, and extraction such as liquid-liquid extraction.

The produced isocyanate group-terminated prepolymer has an isocyanate equivalent of, for example, 80 to 2,000, preferably 100 to 1,000.

Then, to allow the produced isocyanate group-terminated prepolymer to react with the remaining portion of the active hydrogen group-containing component, the isocyanate group-terminated prepolymer and the remaining portion of the active hydrogen group-containing component are formulated (mixed) such that the isocyanate index (NCO concentration/hydroxyl group concentration×100) is, for example, 50 to 200, preferably 75 to 125, and then the mixture is injected into a mold, and curing reaction is conducted at, for example, 0 to 250° C., preferably room temperature (20° C.) to 150° C. for, for example, 1 minute to 7 days, preferably for 10 minutes to 2 days.

In the curing reaction as well, the above-described urethanizing catalyst can be added at the above-described blending ratio. The curing reaction can be conducted in the presence of a known solvent.

The polyurethane resin (molded article, resin sheet) molded into a predetermined shape can be produced, after injecting into a mold and subjecting it to curing reaction, by removing from the mold.

The polyurethane resin can cause birefringence to light (for example, laser light, etc.) passing through inside the molded article due to generation of photoelasticity, that is, stress. Therefore, it can be used suitably as the resin sheet 4.

To the above-described polyurethane resin composition or polyurethane resin (molded article), as necessary, for example, a known additive such as an antifoaming agent, plasticizer, leveling agent, delusterant, fire retardant, thixotropic agent, tackifier, thickening agent, lubricant, antistatic agent, surfactant, reaction retardant, dehydration agent, antioxidant, ultraviolet ray absorber, hydrolysis prevention agent, and weathering stabilizer can be suitably added.

The photoelastic resin used in the resin sheet 4 is not limited to the above-described polyurethane resin, and a known photoelastic resin can be used.

The photoelastic resin has a photoelastic constant at 25° C. of, for example, $1000 \times 10^{-12}$ $Pa^{-1}$ or more, preferably, $2000 \times 10^{-12}$ $Pa^{-1}$ or more, more preferably, $3000 \times 10^{-12}$ Pa$^{-1}$ or more, and for example, 100000×10$^{-12}$ Pa$^{-1}$ or less, preferably 10000×10$^{-12}$ Pa$^{-1}$ or less, more preferably, less than 4000×10$^{-12}$ Pa$^{-1}$.

When the photoelastic constant is more than the above-described lower limit, excellent photoelasticity, particularly excellent photoelasticity that is necessary for the cushion having a sensor 1 can be ensured.

The photoelastic constant of the photoelastic resin can be measured in accordance with the description of "photoelastic constant measurement method" in "development of a system for measuring the photoelastic constants of optical films" in Journal of The Japan Society for Precision Engineering vol. 73, 253-258 (2007) by Mitsuo Tuskiji, Hiroyuki Takada. and Yoshiro Tajitsu.

Along with the measurement of the photoelastic constant, the distortion optical constant and the Young's modulus of the photoelastic resin can be determined.

The distortion optical constant of the photoelastic resin shows the intensity of birefringence generated by the deformation relative to the amount of deformation of the photoelastic resin.

The photoelastic constant, distortion optical constant, and Young's modulus satisfy formula (5) below:

$$\text{Photoelastic constant} = \text{distortion optical constant} \div \text{Young's modulus} \quad (5)$$

Thus, to set the photoelastic constant of the photoelastic resin to the above-described desired range, the distortion optical constant and Young's modulus are adjusted.

To be specific, the higher the distortion optical constant, and the lower the Young's modulus, the higher the photoelastic constant, but when the Young's modulus is excessively low, moldability may be reduced.

Therefore, the photoelastic resin has a Young's modulus at 25° C. of, for example, 0.1 MPa or more, preferably 1 MPa or more, more preferably 2 MPa or more, and for example, 10 MPa or less, preferably 9 MPa or less, more preferably 5 MPa or less.

When the photoelastic resin has a Young's modulus of less than the above-described range, the photoelastic resin may be excessively soft and easily get damaged, and processability may be reduced. When the photoelastic resin has a Young's modulus of more than the above-described range, the photoelastic resin may be excessively hard, and photoelasticity may be reduced.

Preferably, to obtain the above-described desired photoelastic constant, when the photoelastic resin has a Young's modulus at 25° C. of 2 MPa or more and 3 MPa or less, the distortion optical constant at 25° C. is, for example, 6000×10$^{-6}$ or more (generally 10000×10$^{-6}$ or less), and when the photoelastic resin has a Young's modulus at 25° C. of more than 3 MPa and 5 MPa or less, the distortion optical constant at 25° C. is, for example, 10000×10$^{-6}$ or more (generally 20000×10$^{-6}$ or less).

The photoelastic resin has a glass transition temperature of, for example, −60° C. or more, preferably −50° C. or more, more preferably −40° C. or more, and for example, less than 25° C., preferably less than 0° C., more preferably less than −25° C.

When the photoelastic resin has a glass transition temperature of less than the above-described lower limit, processability and scratch resistance of the photoelastic resin may be reduced.

When the glass transition temperature of the photoelastic resin is the above-described upper limit or more, it becomes difficult to obtain the above-described desired photoelastic constant.

To be specific, as described later, when the cushioning material having a sensor 1 is used for, for example, a bed (nursing bed, etc.), the bed is usually set in a room in which the temperature is adjusted to around 20° C. However, by allowing a person (patient, etc.) to lie on the bed, the temperature of the photoelastic resin may be increased to about the temperature of a human body (around 37° C.).

In such a case, when the glass transition temperature of the photoelastic resin is the above-described upper limit or more, the Young's modulus of the resin drastically changes by its temperature. As a result, the sensitivity (photoelastic constant) of the photosensor may drastically change, and the measurement may be inaccurate.

Therefore, it is preferable that the glass transition temperature of the photoelastic resin is in the above-described range.

The glass transition temperature of the photoelastic resin can be obtained by measurement using a dynamic viscoelasticity measuring apparatus with a frequency of 10 Hz and under temperature distribution mode (temperature increase rate 5° C./min).

With the above-described glass transition temperature measurement, the storage modulus E', loss modulus E", and loss tangent tan δ can be obtained at the same time.

The photoelastic resin has a storage modulus E' at 25° C. of, for example, 1×10$^6$ to 1×10$^8$ Pa, a loss modulus E" at 25° C. of, for example, 1×10$^4$ to 1×10$^8$ Pa, and loss tangent tan δ at 25° C. of, for example, 0.01 to 0.2.

The resin sheet 4 made of photoelastic resin is, as shown in FIG. 1, formed into a generally rectangular flat plate shape when viewed in plan view.

The resin sheet 4 has, when the cushioning material having a sensor 1 is used as a bed, a size of about the same as that of the cushioning material 21 (ref: FIG. 2) to be described later, or of a size smaller than the cushioning material 21. To be specific, the size is, for example, length in longitudinal direction of, for example, 10 cm or more, preferably 50 cm or more, and for example, 250 cm or less, preferably 180 cm or less. The length in lateral direction of, for example, 10 cm or more, preferably 50 cm or more, and for example, 200 cm or less, preferably 150 cm or less.

The resin sheet 4 has an area in plan view of, for example, 100 cm$^2$ or more, preferably 500 cm$^2$ or more, and for example, 50000 cm$^2$ or less, preferably 40000 cm$^2$ or less.

The thickness of the resin sheet 4 is not particularly limited, but for example, the thickness is 0.01 mm or more, preferably 0.1 mm or more, more preferably 0.3 mm or more, and for example, 50 mm or less, preferably 10 mm or less, more preferably 5 mm or less.

In FIG. 2, the cushioning material 21 is formed into a generally rectangular flat plate shape when viewed in plan view, and is laminated on one side in thickness direction (upper side on the plane of paper) of the resin sheet 4.

The cushioning material 21 is not particularly limited, and for example, known cushioning materials such as polyurethane resin foam, and polyester resin foam can be used.

These cushioning materials 21 can be used singly, or can be used in combination of two or more.

The cushioning material 21 has, when the cushioning material having a sensor 1 is used as a bed, a size that is about the same as that of the resin sheet 4, or a size that is larger than the resin sheet 4. To be specific, the size is as follows: for example, the length in longitudinal direction is, for example, 50 cm or more, preferably 100 cm or more, and for example, 250 cm or less, preferably 180 cm or less. The length in lateral direction is, for example, 50 cm or more, preferably 100 cm or more, for example, 200 cm or less, preferably 150 cm or less.

The cushioning material 21 has an area in plan view of, for example, 2500 cm$^2$ or more, preferably 5000 cm$^2$ or more, and for example, 50000 cm$^2$ or less, preferably 40000 cm or less, and the ratio of the area in plan view of the cushioning material 21 relative to the area in plan view of the resin sheet 4 is, for example, 100% or more, preferably 150% or more, and for example, 9000% or less, preferably 1000% or less.

The thickness of the cushioning material 21 is not particularly limited, but for example, it is 1 cm or more, preferably 3 cm or more, and for example, 30 cm or less, preferably 20 cm or less.

The photosensor 15 has, as shown in FIG. 1, a light generating unit 5 and a light receiving unit 8 that are disposed to face each other with the resin sheet 4 interposed therebetween so as to overlap with the resin sheet 4 on a projected plane when projected in horizontal direction (direction perpendicular to the thickness direction of the resin sheet 4). To be specific, a photosensor 15 includes a pair of light generating unit 5 and light receiving unit 8 that are provided so as to sandwich the resin sheet 4 from both sides in longitudinal direction, and a pair of light generating unit 5 and light receiving unit 8 that are provided so as to sandwich the resin sheet 4 from both sides in lateral direction.

The light generating unit 5 includes a plurality of longitudinal-side light generating units 6 that are disposed on one side in longitudinal direction of the resin sheet 4 in parallel along the lateral direction, and a plurality of lateral-side light generating units 7 that are disposed on one side in lateral direction of the resin sheet 4 in parallel along the longitudinal direction.

The longitudinal-side light generating units 6 include a first light generating unit 5A, a second light generating unit 5B, and a third light generating unit 5C that are disposed sequentially from the other side to one side in lateral direction. The lateral-side light generating units 7 include a fourth light generating unit 5D, a fifth light generating unit 5E, and a sixth light generating unit 5F that are disposed sequentially on one side to the other side in longitudinal direction.

The light generating unit 5 is not particularly limited, and for example, a semiconductor laser (wavelength 405 nm to 1064 nm), a light-emitting diode, a fluorescent lamp, a halogen lamp, and a tungsten lamp are used.

The light receiving unit 8 is provided in correspondence with light generating unit 5 so that the light generated from the light generating unit 5 is received through the resin sheet 4, and includes longitudinal-side light receiving unit 9 and lateral-side light receiving unit 10 that are disposed to face the longitudinal-side light generating unit 6 and the lateral-side light generating unit 7 so as to sandwich the resin sheet 4 with the longitudinal-side light generating unit 6 and the lateral-side light generating unit 7.

The plurality of longitudinal-side light receiving units 9 are disposed in parallel along the lateral direction on the other side in longitudinal direction of the resin sheet 4. That is, the longitudinal-side light receiving units 9 include, in correspondence with the first light generating unit 5A, the second light generating unit 5B, and the third light generating unit 5C, a first light receiving unit 8A, a second light receiving unit 8B, and a third light receiving unit 8C that are disposed from the other side to one side in lateral direction sequentially.

The plurality of lateral-side light receiving units 10 are disposed in parallel along longitudinal direction on the other side in lateral direction of the resin sheet 4. That is, the lateral-side light receiving unit 10 include, in correspondence with the fourth light generating unit 5D, the fifth light generating unit 5E, and the sixth light generating unit 5F, a fourth light receiving unit 8D, a fifth light receiving unit 8E, and a sixth light receiving unit 8F that are disposed from one side to the other side in vertical direction sequentially.

The light receiving unit 8 is not particularly limited, but for example, a sensor such as, for example, silicon photodiode is used.

In this manner, on the line connecting the light generating unit 5 and the light receiving unit 8 on the resin sheet 4, to be specific, on the intersection of the line connecting the longitudinal-side light generating unit 6 and the longitudinal-side light receiving unit 9 and the line connecting the lateral-side light generating unit 7 and the lateral-side light receiving unit 10, a plurality of (9) detection portions (shown in solid line and broken line circles) 11 (11a to 11i) are defined for detecting the pressure when pressed.

In the cushioning material having a sensor 1, a plurality of (4) polarizing plates 13 interposed between the resin sheet 4, and the light generating unit 5 and the light receiving unit 8 are provided. To be specific, the polarizing plate 13 is disposed, between the resin sheet 4 and the longitudinal-side light generating unit 6, between the resin sheet 4 and the lateral-side light generating unit 7, between the resin sheet 4 and the longitudinal-side light receiving unit 8, and between the resin sheet 4 and the lateral-side light generating unit 9.

To be specific, the polarizing plate 13 consists of, a polarizer disposed between the resin sheet 4 and the longitudinal-side light generating unit 6, a polarizer disposed between the resin sheet 4 and the lateral-side light generating unit 7, an analyzer disposed between the resin sheet 4 and the longitudinal-side light receiving unit 8, and an analyzer disposed between the resin sheet 4 and the lateral-side light receiving unit 9.

In this manner, the light generated from the light generating unit 5 is converted by the polarizer into linearly polarized light or circularly polarized light, passes through the resin sheet 4, and reaches the analyzer.

At this time, the polarizer and the analyzer are set so that the intensity of light passing through the analyzer is the minimum while no load is applied on the resin sheet 4.

To be specific, they are set so that the angle formed between the polarized vibration plane of the polarizer and the polarized vibration plane of the analyzer is 90 degrees. When the polarizing plate is a circular polarizing plate, a circular polarizing plate having different rotation direction among the polarizer and the analyzer is used. That is, when the polarizer is a right circular polarizing plate, a left circular polarizing plate is used for the analyzer.

Examples of the polarizing plate 13 include a glass-made polarizing plate, a resin-made linear polarizing plate, and a circular polarizing plate. When the light generating unit 5 is a light source that generates linearly polarized light, such as a semiconductor laser, the polarizer between the light generating unit 5 and the resin sheet 4 can be omitted. When the light generated from the light generating unit 5 is not sufficiently polarized (when light-emitting diode or fluorescent lamp is used as the light generating unit 5), preferably, the polarizer is used.

The processor 3 is provided to detect the stress applied to the resin sheet 4 based on the light signal detected by the photosensor 15.

To be specific, the processor 3 includes, for example, a LED 14, and is electrically connected through the light receiving units 8 and wiring 12. The processor 3 detects presence or absence of the stress at the detection portion 11 of the resin sheet 4 based on the detection signal of birefringence of the laser light detected at the longitudinal-side light receiving unit 9 and the detection signal of the birefringence of the laser light detected at the lateral-side light receiving unit 10, and shows it on the LED 14.

Next, a method (in the following, may be referred to as detection method 1) for sensing the stress using the cushioning material having a sensor 1 is described with reference to FIG. 1.

First, in the photosensor 15, laser light is allowed to exit from the light generating unit 5 to the light receiving unit 8 so as to pass through inside the resin sheet 4. At this time, in the resin sheet 4, birefringence is not caused in the laser light, and therefore laser light is blocked with the polarizing plate 13, and the light receiving unit 8 receives no light.

Then, stress is generated at the detection portion 11 of the resin sheet 4. This causes birefringence at the detection portion 11, and therefore the light receiving unit 8 receives the laser light that went through birefringence.

To be specific, the first light receiving unit 8A and the fourth light receiving unit 8D disposed at the other side in longitudinal direction of the detection portion 11a and the other side in lateral direction of the detection portion 11a detect the presence or absence of birefringence at the detection portion 11a.

Then, electric signals based on detection of birefringence at the first light receiving unit 8A and the fourth light receiving unit 8D are inputted to the processor 3, and in this manner, the processor 3 detects that the stress generated portion is detection portion 11a.

Other detection portions 11 (11b to 11i) also detect the stress generated portion in the same manner as described above.

With the cushioning material having a sensor 1, the pressure can be detected easily and precisely.

That is, when, for example, a piezoelectric film is used for pressure detection, there was a disadvantage in that correction with temperature was necessary, and also there was a disadvantage in that the changes in the temperature is wrongly detected as a pressure. Furthermore, the piezoelectric film generates an electric signal in accordance with changes in the pressure, but when the pressure is constant, the electric signal is not generated. Therefore, to grasp the pressure status continuously using the piezoelectric film, there was a disadvantage in that complicated processing such as time integration of the signal intensity was necessary.

Meanwhile, with the above-described cushioning material having a sensor 1, light generated from the light generating unit 5 passes through inside the resin sheet 4 composed of photoelastic resin at the stress-applied portion, and then received by the light receiving unit 8, and this allows the processor 3 to detect the stress at the resin sheet 4.

Therefore, with the above-described cushioning material having a sensor 1, without correction with temperature, or even under a constant pressure, the pressure can be detected easily and precisely.

The method for sensing the stress using the cushioning material having a sensor 1 is not limited to the one described above, and other sensing methods can also be used.

To be more specific, in the above-described method (detection method 1), the polarizer and the analyzer are set so that the intensity of light passing through the analyzer under no load to the resin sheet 4 is the minimum, and the intensity of light the light receiving unit 8 receives increases in accordance with the stress generated portion.

Meanwhile, in the method (in the following, may be referred to as detection method 2) below, for example, the polarizer and the analyzer are set so that the light intensity passing through the analyzer is the maximum when there is no load on the resin sheet 4.

That is, when the detection method 2 is used, settings are made so that the angle between the polarized vibration plane of the polarizer and the polarized vibration plane of the analyzer is preferably, 0 degree.

When the polarizing plate is a circular polarizing plate, circular polarizing plates having the same rotation direction of circular polarization are used for the polarizer and the analyzer. That is, when the polarizer is a right circular polarizing plate, a right circular polarizing plate is used for the analyzer.

In this manner, in the detection method 2, unlike the above-described detection method 1, generation of stress reduces the intensity of light passing through the analyzer. That is, the intensity of light received by the light receiving unit 8 decreases in accordance with the portion where stress is generated. Then, the electric signal based on the detection is inputted to the processor 3, and the processor 3 detects the stress generated portion.

The pressure can be detected easily and precisely by such a method as well.

Furthermore, although it is not shown, the polarizer and the analyzer can also be omitted.

To be more specific, when this detection method (in the following, may be referred to as detection method 3) is used, no polarizer or analyzer is provided in the cushion having a sensor 1.

In the cushion having a sensor 1, unlike the detection method 1 and the detection method 2, the light outputted from the light generating unit 5 and propagated through the resin sheet 4 enters the light receiving unit 8 without going through the analyzer.

In such a case, when a load is applied to the resin sheet 4, birefringence is caused in accordance with the load, and the birefringence causes the optical path of the light propagating through the resin sheet 4 to bend radially.

As a result, a portion of light slips out of the resin sheet 4 from the portion where the load was applied, and the quantity of light propagating decreases in accordance with the load.

Then, the light receiving unit 8 detects the changes in the quantity of light, and the electric signal based on the detection is inputted to the processor 3. The processor 3 detects (measures) the stress-generated portion and the size of the load in this manner.

The pressure can be detected easily and precisely by such a method as well.

Figure 3:
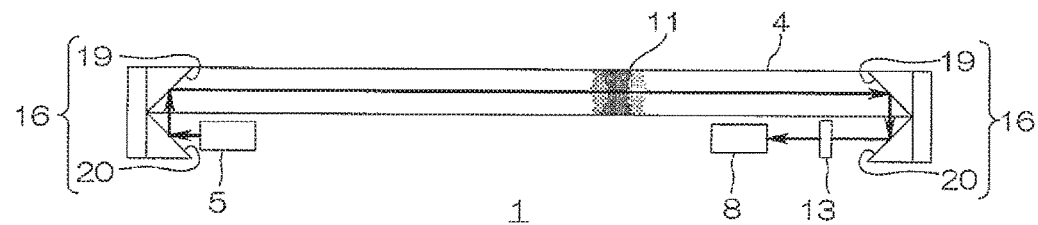
FIG. 3 shows a cross sectional view of the cushioning material having a sensor in another embodiment of the present invention (embodiment in which the light generating unit and the light receiving unit are disposed inside the resin sheet).

In the above-described embodiment, both of the light generating unit 5 and the light receiving unit 8 are provided outside of the resin sheet 4 when viewed in plan view, but their dispositions are not particularly limited, and for example, as shown in FIG. 3, they can be provided inside the resin sheet 4.

In FIG. 3, a mirror 16 is provided at the peripheral end portions of the resin sheet 4. The mirror 16 is disposed next to the resin sheet 4 outside in longitudinal direction and lateral direction, and includes an upper mirror plane 19 that is disposed to incline outside at a degree of about 45 as it approaches the lower side, and a lower mirror plane 20 disposed continuously at a lower end portion of the upper mirror plane 19 to incline inside at a degree of about 45 as it approaches the lower side.

The light generating unit 5 is disposed at a lower side of the resin sheet 4 for pressure-sensitive sensor to be spaced apart from the lower mirror plane 19 at the inside (the other side in longitudinal direction and the other side in lateral direction, ref: FIG. 1).

The light receiving unit 8 is disposed at the lower side of the resin sheet 4 for pressure-sensitive sensor with the polarizing plate 13 interposed therebetween to be spaced apart from the lower mirror plane 19 at the inside (one side in longitudinal direction and one side in lateral direction, ref: FIG. 1).

In this cushioning material having a sensor 1, when a stress is generated in the resin sheet 4, birefringence is generated at the detection portion 11, and the laser light that went through birefringence is reflected at the mirror 16. Thereafter, the reflected light is received by the light receiving unit 8. In this manner, the processor 3 (ref: FIG. 1) detects the stress at the detection portion 11.

In this cushioning material having a sensor 1, the light generating unit 5 and the light receiving unit 8 are provided inside the resin sheet 4, and therefore a small size can be achieved.

The disposition of the light generating unit 5 and the light receiving unit 8 is not limited to the one described above, and for example, as shown in FIG. 4, the light receiving unit 8 can be disposed at the cushioning material 21 side in the lamination direction of the resin sheet 4 and the cushioning material 21, to be specific, the light receiving unit 8 can be disposed at the lower side of the resin sheet 4.

Figure 4:
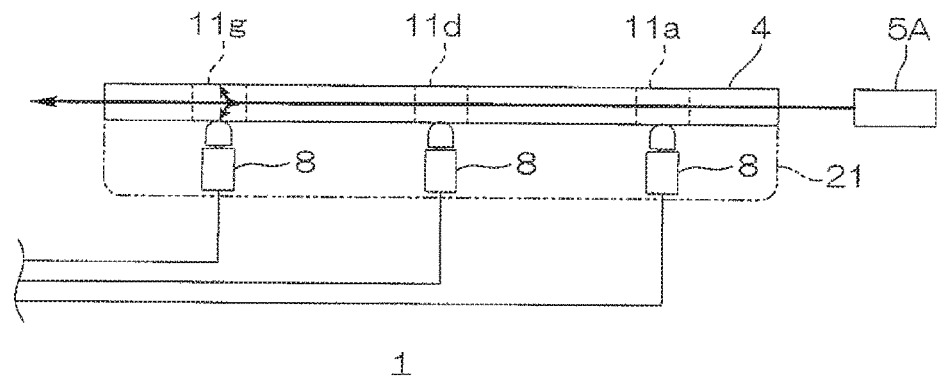
FIG. 4 shows a cross sectional view of the cushioning material having a sensor in another embodiment of the present invention (embodiment in which the light receiving unit is disposed below the resin sheet).

In FIG. 4, the light generating unit 5 is disposed so as to overlap with the resin sheet 4 on the plane of projection when projected in horizontal direction (direction perpendicular to the thickness direction of the resin sheet 4) (ref: FIG. 1).

The light receiving unit 8 is provided in a number that is the same as the number of, for example, the detection portion 11 (in FIG. 1, 9 (11*a* to 11*i*)).

The light receiving unit 8 is disposed at the lower portion of the resin sheet 4. That is, the light receiving units 8 are disposed so as to overlap with the resin sheet 4 at the plane of projection when the resin sheet 4 is projected in thickness direction. To be specific, the light receiving unit 8 is disposed so as to overlap with the detection portion 11 of the resin sheet 4 in correspondence with the detection portion 11, and is embedded in the cushioning material 21.

In such a case, when a load is applied to the resin sheet 4, birefringence is caused in accordance with the load, and the birefringence causes the optical path of the light propagating through the resin sheet 4 to bend radially.

As a result, a portion of light slips out of the resin sheet 4 from the portion where the load was applied, and the light receiving unit 8 corresponding to the stress generated portion (for example, detection portion 11*a* (ref: FIG. 1)) detects the light.

Changes in quantity of light is detected by the light receiving unit 8 in this manner, and the electric signal based on the detection is inputted to the processor 3, and the processor 3 detects (measures) the stress generated portion and the load intensity.

The pressure can be detected easily and precisely by such a method as well.

Such a cushioning material having a sensor 1 can be suitably used in various fields in which pressure detection is required, for example, a bed, sofa, chair, and seats of, for example, automobiles and airplanes in various industrial fields. Preferably, the cushioning material having a sensor 1 is used for a bed.

In the following, a bed including the above-described cushioning material having a sensor 1 is described with reference to FIG. 5.

Figure 5:
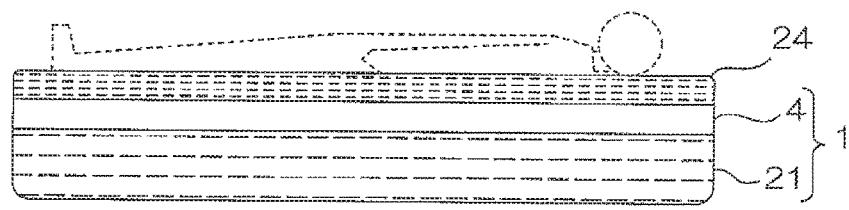
FIG. 5 shows a side view of the bed in one embodiment of the present invention (embodiment in which the cushioning material is not divided).

In FIG. 5, a bed 25 includes the above-described cushioning material having a sensor 1 and bedding 24.

The bedding 24 is, for example, a futon, and is laminated on one side in thickness direction (upper side on the plane of paper) of the resin sheet 4 of the cushioning material having a sensor 1.

In such a bed 25, the cushioning material 21 of the cushioning material having a sensor 1 supports the weight of a person as a mattress, and the weight is applied on the resin sheet 4 as a stress.

Figure 6A:
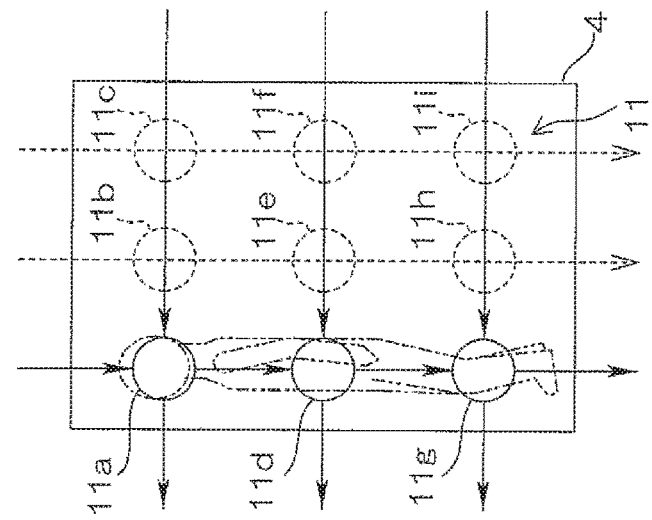
FIG. 6 shows a plan view illustrating a state where a human body is lying on the bed shown in FIG. 5, FIG. 6A illustrating a state where the human body is lying on a center portion of the bed, FIG. 6B illustrating a state where the human body is lying on a right side portion of the bed, and FIG. 6C illustrating a state where the human body is lying on a left side portion of the bed.

To be more specific, as shown with the broken line in FIG. 5, when a human body is lying on the center of the bed 25, on the resin sheet 4, as shown in FIG. 6A, the detection portions 11*b*, 11*e*, and 11*h* shown in the solid line detect the stress, and the detection portions 11*a*, 11*c*, 11*d*, 11*f*, 11*g*, and 11*i* shown in the broken line do not detect stress.

Figure 6B:
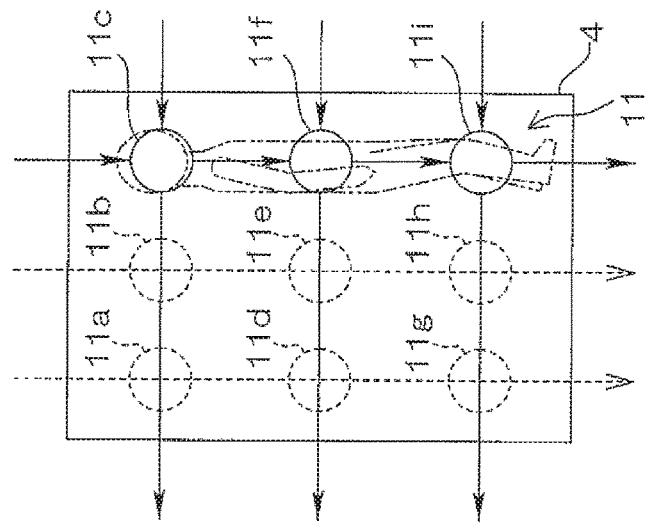

Then, as shown in FIG. 6B, when the human body moves to the right side on the plane of the paper by, for example, turning, the stress detected by the detection portions 11*b*, 11*e*, and 11*h* decreases, and stress is detected newly by the detection portions 11*c*, 11*f*, and 11*i*.

Figure 6C:
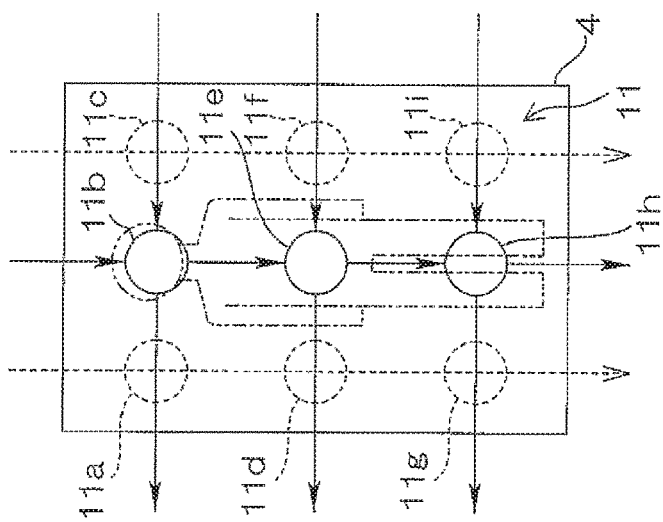

Similarly, as shown in FIG. 6C, when the human body moves to the left side on the plane of the paper by turning, the stress detected by the detection portions 11*b*, 11*e*, and 11*h* decreases, and stress is detected newly by the detection portions 11*a*, 11*d*, and 11*g*.

By monitoring increases and decreases of the stress at the detection portions, movement of the human body on the bed 25 by, for example, turning can be detected.

Furthermore, when the person is lying at the position of, for example, FIG. 6A, and the person lifts his/her upper body on the bed 25, stress is not detected by the detection portion 11*b*, and the detection portions 11*e* and 11*h* detect the stress. That is, by monitoring the decrease and increase of stress at the detection portions, it can be detected that the person lying on the bed 25 got up.

In such a bed 25, the above-described cushioning material having a sensor 1 is used, and therefore the light generated from the light generating unit 5 passes through inside the resin sheet 4, and thereafter received by the light receiving unit 8, and the processor 3 detects the stress at the resin sheet 4.

Therefore, with the above-described bed 25, without correction with temperature, and even under a constant pressure, the pressure can be detected easily and precisely.

Figure 7:
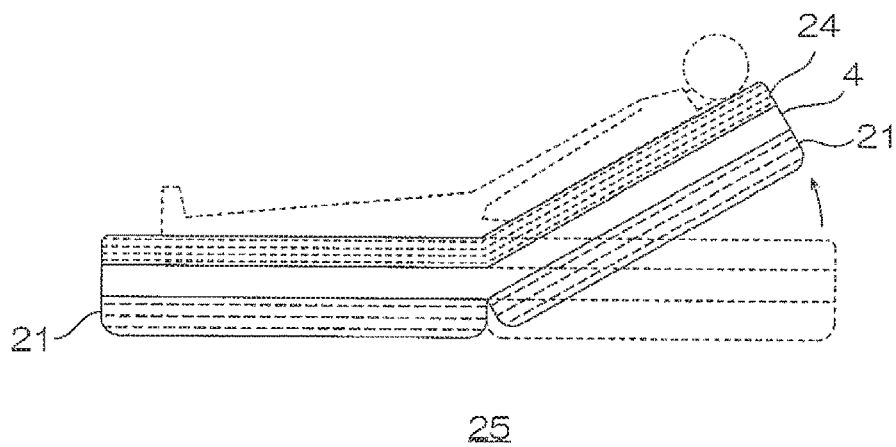
FIG. 7 shows a side view of the bed in another embodiment of the present invention (embodiment in which the cushioning material is divided into two and is bent).
Figure 8:
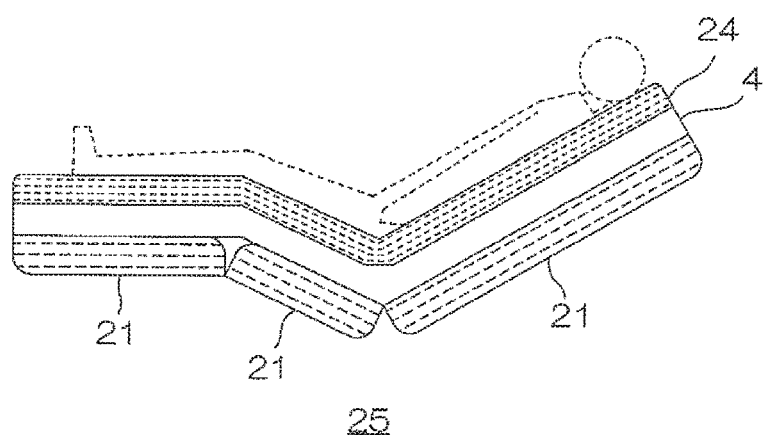
FIG. 8 shows a side view of the bed in another embodiment of the present invention (embodiment in which the cushioning material is divided into three and is bent, and the resin sheet is laminated on the entire cushioning material).

In particular, the above-described resin sheet 4 is flexible and can keep polarization even when it is bent, and therefore the above-described cushioning material having a sensor 1 is suitably used when the resin sheet 4 is required to be bent, to be specific, as shown in FIG. 7 and FIG. 8, it is suitably used for a bed (nursing bed, medical bed, etc.) having a mechanism in which the cushioning material 21 (mattress) is divided and bent to support the care receiver's eating and getting up.

Figure 9:
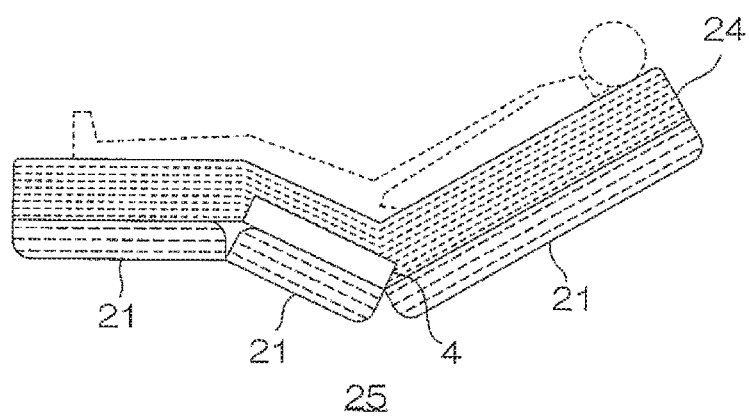
FIG. 9 shows a side view of the bed in another embodiment of the present invention (embodiment in which the cushioning material is divided into three and is bent, and the resin sheet is laminated on a portion of the cushioning material).

In such a case, the resin sheet 4 can be laminated on the entire cushioning material 21, as shown in FIG. 7 and FIG. 8, or can be laminated only on a portion of the cushioning material 21 (for example, one of the cushioning material 21 divided into a plural number), as shown in FIG. 9.

Furthermore, although not shown, the cushioning material 21 will suffice as long as it is laminated on the resin sheet 4, and for example, the cushioning material 21 can be laminated on both sides in the thickness direction of the resin sheet 4, and the resin sheet 4 can be disposed inside the cushioning material 21 (mattress), the resin sheet 4 can be laminated only on the upper face or the lower face in the thickness direction of the cushioning material 21 (mattress). Furthermore, other layers can be interposed between the resin sheet 4 and the cushioning material 21. Furthermore, for example, a protection sheet composed of a known resin can be attached to one side or both sides of the resin sheet 4.

In the description above, nine detection portions 11 are defined, but the number of the detection portions is not particularly limited, and the number can be suitably designed in accordance with the number of the light generating unit 5 and the light receiving unit 8. For example, by setting the number of the lateral-side light generating unit 7 and the lateral-side light receiving unit 10 to four each, 12 detection portions 11 can be defined, and detection precision can be improved.

The cushioning material having a sensor 1 can also be used, for example, for a load sensor.

Figure 10:
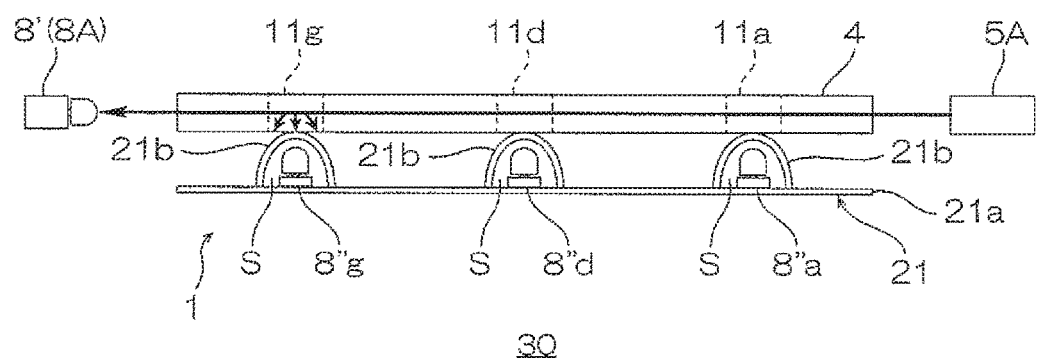
FIG. 10 shows a side view of the bed in another embodiment of the present invention (embodiment in which the light receiving unit is disposed to face the light generating unit, and is disposed also below the resin sheet).

In such a case, as shown in FIG. 10, the light receiving unit 8 is disposed to face the light generating unit 5, and furthermore, also disposed at the lower portion of the resin sheet 4 (the cushioning material 21 side in the lamination direction of the resin sheet 4 and the cushioning material 21).

To be more specific, in the load sensor 30, the light generating unit 5 and the light receiving unit 8 are disposed to face each other with the resin sheet 4 interposed therebetween on projection plane when projected in horizontal direction (direction perpendicular to thickness direction of the resin sheet 4) to overlap with the resin sheet 4 (ref: FIG. 1).

In the following, the light receiving unit 8 disposed to face the light generating unit 5 is referred to as a counter light receiving unit 8'.

In FIG. 10, the first light receiving unit 8A (ref: FIG. 1) disposed to face the first light generating unit 5A (ref: FIG. 1) is noted as a counter light receiving unit 8'.

Furthermore, in FIG. 10, a light receiving unit 8 is disposed at the lower portion of the resin sheet 4 as well. In the following, the light receiving unit 8 disposed at the lower portion of the resin sheet 4 is referred to as a lower side light receiving unit 8".

In FIG. 10, the lower-side light receiving unit 8" is provided in a number that is the same as the number of the detection portion 11 (in FIG. 1, nine (11a to 11i)).

The lower-side light receiving units 8" are disposed, on projection plane when the resin sheet 4 is projected in thickness direction, so as to overlap with the resin sheet 4. To be specific, the lower-side light receiving units 8" are disposed so as to overlap with the detection portion 11 of the resin sheet 4 in correspondence with the detection portion 11. In the following, the lower-side light receiving units 8" are noted as the lower-side light receiving unit 8"a to 8"i in correspondence with the detection portion 11a to 11i.

In FIG. 10, only the lower-side light receiving unit 8"a corresponding to the detection portion 11a, the lower-side light receiving unit 8"d corresponding to the detection portion 11d, and the lower-side light receiving unit 8"g corresponding to the detection portion 11 g are shown.

The cushioning material 21 is composed of a flexible resin sheet (for example, polypropylene sheet, polyethylene sheet, etc.), and has a plate member 21a that is generally rectangular when viewed in plan view and a protrusion member 21b that is a generally hemispherical plate.

The thickness of the plate member 21a is not particularly limited, and is set suitably in accordance with its use and purpose.

The protrusion member 21b is provided in the same number as the number of the lower-side light receiving unit 8", and is disposed at one side of the plate member 21a (to be specific, the resin sheet 4 side in lamination direction of the resin sheet 4 and the cushioning material 21) so as to protrude from one side of the plate member 21a.

The protrusion height of the protrusion members 21b is not particularly limited, and is set suitably in accordance with use and purpose, and for example, 1 to 2 cm.

Such protrusion members 21b are disposed in accordance with the lower-side light receiving units 8", and an accommodation unit S having a protruded hollow structure is formed to accommodate the lower-side light receiving unit 8".

The accommodation unit S is a space defined with the protrusion member 21b, and accommodates the lower-side light receiving unit 8". The accommodation unit S can be hollow, but preferably, the inside the accommodation unit S is charged with a soft resin (for example, elastomer, gel, etc.).

In such a load sensor 30, generally, light emitted from the light generating unit 5 passes through the resin sheet 4, and enters a counter light generating unit 8'.

Then, when a load is applied on the resin sheet 4, in accordance with the stress at the contact portion between the resin sheet 4 and the cushioning material 21, birefringence is caused and the birefringence causes the optical path of the light propagating through the resin sheet 4 to bend radially.

As a result, a portion of light slips out of the resin sheet 4, and the light enters into the lower-side light receiving unit 8"a corresponding to the stress generated portion (for example, detection portion 11a (ref: FIG. 1)).

That is, the quantity of light detected at the lower-side light receiving unit 8" is generally proportional to the size of the load (stress) on the resin sheet. Meanwhile, the quantity of light detected at the counter light receiving unit 8' is inversely proportional to the size of the load (stress) on the resin sheet.

Therefore, by analyzing data on the quantity of light at the counter light receiving unit 8', the size of the load (stress) can be determined. For example, when a person gets on the resin sheet 4, the above-described analysis can determine the weight of the person.

Furthermore, also by analyzing the data on the quantity of light of the lower-side light receiving unit 8", the size of the load (stress) can be determined.

Furthermore, by analyzing the data on the quantity of light of the lower-side light receiving unit 8", load distribution (stress distribution) can be determined. For example, when a person gets on the resin sheet 4, the above-described analysis can determine the load distribution of the sole, and furthermore, the position and changes over time (staggering) of the barycenter can be determined, and therefore can be used for determination of health status.

Figure 11:
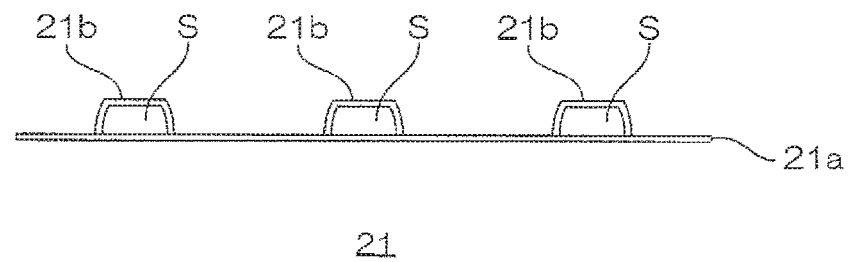
FIG. 11 shows a side view of the cushioning material shown in FIG. 10 in another embodiment (embodiment in which the protrusion member is generally trapezoid when viewed in cross section).

In the description above, the protrusion member 21b is semispherical. However, the shape of the protrusion member 21b is not particularly limited, and for example, as shown in FIG. 11, the contact face with the resin sheet 4 can also be flat (that is, generally trapezoid when viewed in cross section).

For the light receiving unit, the counter light receiving unit 8' can be omitted and only the lower-side light receiving unit 8" can be set.

The cushioning material having a sensor of the present invention can be set on the floor beside the bed for the purpose of detecting if the care receiver is off the bed and on the floor. Furthermore, by disposing the cushioning material having a sensor of the present invention on the entire floor of a bedroom, movement of the care receiver in the room can be monitored. By disposing the cushioning material having a sensor of the present invention on the floor of a bathroom floor, the movement of the care receiver from the bathtub to the floor can be detected. Also, the cushioning material having a sensor of the present invention can be used for various purposes, for example, by disposing the cushioning material having a sensor of the present invention on indoor corridor, passing of pedestrians can be detected, or by disposing the cushioning material having a sensor of the present invention at the entrance of a room, a person entering the room can be detected.

EXAMPLES

In the following, the present invention is described based on Reference Examples, but the present invention is not limited to Reference Examples below. "Parts" and "%" are based on mass unless otherwise specified in the following. The specific numeral values in Reference Examples can be replaced with the numeral values (that is, upper limit value or lower limit value) used in DESCRIPTION OF EMBODIMENTS.

Reference Example 1 (Production of Resin Sheet 1)

A glass-made flask was charged with 100 parts by mass of polytetramethylene ether glycol (Hodogaya Chemical Co., Ltd., PTG-650SN, hydroxyl number 174.9 mgKOH/g), and 1 part by mass of an antioxidant, the mixture was dried under reduced pressure at 120° C. for 2 hours, and the pressure was set back to normal pressure with nitrogen. Then, while stirring, 2.25 parts by mass of 1,3-propanediol and 0.6875 parts by mass of 1,2,6-hexanetriol were added, and the temperature was increased to 70° C. Then, a few drops of an antifoaming agent were added, and 48.75 parts by mass of 4,4'-diphenylmethane diisocyanate (Mitsui Chemicals, MDI-PH) melted at 70° C. was added therein, and the mixture was stirred. Thereafter, defoaming was conducted under reduced pressure for 30 seconds, and the pressure was set back to normal pressure with nitrogen. Thereafter, it was poured into a mold from the flask, and curing was conducted at 70° C. for 18 hours, thereby producing a resin sheet (molded article) 1 composed of the polyurethane resin and having a thickness of 2 mm.

The molded article 1 had a photoelastic constant (25° C.) of $5210 \times 10^{-12}$ $Pa^{-1}$, a Young's modulus (25° C.) of 5.04 MPa, and a glass transition temperature of −5° C. measured by the evaluation method described later.

Reference Example 2 (Production of Resin Sheet 2)

A glass-made flask was charged with 100 parts by mass of polytetramethylene ether glycol (Hodogaya Chemical Co., Ltd., PTG-650SN, hydroxyl number 174.9 mgKOH/g), and 1 part by mass of an antioxidant, the mixture was dried under reduced pressure at 120° C. for 2 hours, and the pressure was set back to normal pressure with nitrogen. Then, while stirring, 2.29 parts by mass of 1,3-propanediol and 0.7 parts by mass of 1,2,6-hexanetriol were added, and the temperature was increased to 70° C. Then, a few drops of an antifoaming agent were added, and 50.85 parts by mass of 4,4'-diphenylmethane diisocyanate (Mitsui Chemicals, MDI-PH) melted at 70° C. and 10 parts by mass of 4-cyano-4'-pentylbiphenyl (5CB) were added therein, and the mixture was stirred. Thereafter, defoaming was conducted under reduced pressure for 30 seconds, and the pressure was set back to normal pressure with nitrogen. Thereafter, it was poured into a mold from the flask, and curing was conducted at 70° C. for 18 hours, thereby producing a resin sheet (molded article) 2 composed of the polyurethane resin and having a thickness of 2 mm.

The molded article 2 had a photoelastic constant (25° C.) of $6110 \times 10^{-12}$ $Pa^{-1}$, a Young's modulus (25° C.) of 3.94 MPa, and a glass transition temperature of −10° C. measured by the evaluation method to be described later.

Reference Example 3 (Production of Resin Sheet 3)

A glass-made flask was charged with 100 parts by mass of polytetramethylene ether glycol (Hodogaya Chemical Co., Ltd., PTG-650SN, hydroxyl number 174.9 mgKOH/g), and 1 part by mass of an antioxidant, the mixture was dried under reduced pressure at 120° C. for 2 hours, and the pressure was set back to normal pressure with nitrogen. Then, 0.7 parts by mass of 1,2,6-hexanetriol was added, and the temperature was increased to 70° C. Then, a few drops of an antifoaming agent were added, and 43 parts by mass of 4,4'-diphenylmethane diisocyanate (Mitsui Chemicals, MDI-PH) melted at 70° C., and 10 parts by mass of 4-pentylbiphenyl were added therein, and the mixture was stirred. Thereafter, defoaming was conducted under reduced pressure for 30 seconds, and the pressure was set back to normal pressure with nitrogen. Thereafter, it was poured into a mold from the flask, and curing was conducted at 70° C. for 18 hours, thereby producing a resin sheet (molded article) 3 composed of the polyurethane resin and having a thickness of 2 mm.

The molded article 3 had a photoelastic constant (25° C.) of $5170 \times 10^{-12}$ $Pa^{-1}$, a Young's modulus (25° C.) of 4.18 MPa, and a glass transition temperature of −20° C. measured by the evaluation method described later.

Reference Example 4 (Production of Resin Sheet 4)

A glass-made flask was charged with 100 parts by mass of polycarbonatediol (Daicel Corporation., PLACCELCD 205PL, hydroxyl number 224.7 mgKOH/g), and 1 part by mass of an antioxidant, the mixture was dried under reduced pressure at 120° C. for 2 hours, and the pressure was set back to normal pressure with nitrogen. Then, 0.888 parts by mass of 1,2,6-hexanetriol was added and the temperature was increased to 70° C. Then, a few drops of an antifoaming agent were added, and 55.25 parts by mass of 4,4'-diphenylmethane diisocyanate (Mitsui Chemicals, MDI-PH) melted at 70° C., and 13.6 parts by mass of 4-cyano-4'-pentylbiphenyl (5CB) were added therein, and the mixture was stirred. Thereafter, defoaming was conducted under reduced pressure for 30 seconds, and the pressure was set back to normal pressure with nitrogen. Thereafter, it was poured into a mold from the flask, and curing was conducted at 70° C. for 18 hours, thereby producing a resin sheet (molded article) 4 composed of the polyurethane resin and having a thickness of 2 mm.

The molded article 4 had a photoelastic constant (25° C.) of $6200 \times 10^{-12}$ $Pa^{-1}$, a Young's modulus (25° C.) of 3.99

MPa, and a glass transition temperature of 25° C. measured by the evaluation method described later.

Reference Example 5 (Production of Resin Sheet 5)

(5-1) Synthesis of Polyurethane Polyol (Hydroxyl Group-Terminated Prepolymer) and Polyol Mixture A glass-made flask was charged with 100 parts by mass of polytetramethylene ether glycol (Hodogaya Chemical Co., Ltd., PTG-650SN, hydroxyl number 164.8 mgKOH/g), and 1 part by mass of an antioxidant, and the mixture was dried under reduced pressure at 120° C. for 2 hours, and the pressure was set back to normal pressure with nitrogen. Then, the temperature was increased to 80° C. and 14 parts by mass of 3,3'-dimethylbiphenyl-4,4'-diisocyanate (NISSO SHOJI CO., LTD., TODI) was added while stirring. Reaction was conducted for 3 hours, and it was confirmed with IR measurement that absorption spectrum of NCO group disappeared.

Polyurethane polyol (hydroxyl group-terminated prepolymer) was obtained in this manner.

Then, the temperature was increased to 80° C., and 4 parts by mass of neopentyl glycol, and 5 parts by mass of trimethylolpropane were added. The mixture was stirred for 1 hour for dissolving, thereby producing a polyol mixture. The produced hydroxyl group-terminated prepolymer had an isocyanate index of 35.

(5-2) Curing Reaction

The polyol mixture of the above-described (5-1) was heated to 70° C., and a few drops of an antifoaming agent were added, 49.8 parts by mass of 4,4'-diphenylmethane diisocyanate (Mitsui Chemicals, MDI-PH) melted at 70 was added therein, and the mixture was stirred. Defoaming was conducted under reduced pressure for 30 seconds, and the pressure was set back to normal pressure with nitrogen. Thereafter, it was poured into a mold from the flask, and curing was conducted at 70° C. for 18 hours, thereby producing a resin sheet (molded article) 5 composed of the polyurethane resin and having a thickness of 2 mm.

The molded article 5 had a photoelastic constant (25° C.) of 6280×10−12 Pa$^{-1}$, a Young's modulus (25° C.) of 5.69 MPa, and a glass transition temperature of 19° C. measured by the evaluation method described later.

Reference Example 6 (Production of Resin Sheet 6)

(6-1) Synthesis of Isocyanate Group-Terminated Prepolymer

A glass-made flask was charged with 100 parts by mass of polytetramethylene ether glycol (Hodogaya Chemical Co., Ltd., PTG-650SN, hydroxyl number 164.8 mgKOH/g) and 0.2 parts by mass of an antioxidant, the mixture was dried under reduced pressure at 120° C. for 2 hours, and the pressure was set back to normal pressure with nitrogen. Then, the temperature was increased to 80° C., and 18.3 parts by mass of 3,3'-dimethylbiphenyl-4,4'-diisocyanate (NISSO SHOJI CO., LTD., TODI), and 67.7 parts by mass of 4,4'-diphenylmethane diisocyanate (Mitsui Chemicals, MDI-PH) were added while stirring. Reaction was conducted for 3 hours, thereby producing an isocyanate group-terminated prepolymer. The produced isocyanate group-terminated prepolymer had an isocyanate index of 231.

(6-2) Curing Reaction

The isocyanate group-terminated prepolymer of the above-described (6-1) was heated to 70° C. To 42.9 parts by mass of polytetramethylene ether glycol (Hodogaya Chemical Co., Ltd., PTG-650SN, hydroxyl number 164.8) pre-dried in another flask, 6.55 parts by mass of 3-methyl-1,5-pentanediol, 7.15 parts by mass of trimethylolpropane-ethyleneoxide adduct (Mitsui Chemicals, IR-94, hydroxyl number 920), and 2.32 parts by mass of 2-ethyl-1-hexanol were added, the mixture was stirred well, and the temperature was increased to 70° C.

Then, the above-described mixture was added to the isocyanate group-terminated prepolymer, a few drops of an antifoaming agent were added, and the mixture was stirred. Thereafter, defoaming was conducted under reduced pressure for 30 seconds, and the pressure was set back to normal pressure with nitrogen. Thereafter, it was poured into a mold from the flask, and curing was conducted at 70° C. for 18 hours, thereby producing a resin sheet (molded article) 6 composed of the polyurethane resin and having a thickness of 2 mm.

The molded article 6 had a photoelastic constant (25° C.) of 6700×10$^{-12}$ Pa$^{-1}$, a Young's modulus (25° C.) of 3.32 MPa, and a glass transition temperature of 7° C. measured by the evaluation method described later.

Evaluation

<Photoelastic Constant and Young's Modulus>

Measurement was conducted in accordance with description of "photoelastic constant measurement method" in "development of a system for measuring the photoelastic constants of optical films" in Journal of The Japan Society for Precision Engineering vol. 73, 253-258 (2007) by Mitsuo Tuskiji, Hiroyuki Takada, and Yoshiro Tajitsu" to obtain distortion optical constant and Young's modulus at 25° C., and photoelastic constant at 25° C. was calculated therefrom. For the above-described measurement, laser light having a wavelength of 630 nm was used.

<Dynamic Viscoelasticity>

A sample piece was cut into a strip of a length of 2.5 cm, a width of 5.0 mm, and a thickness of 2.0 mm. The sample was measured using a dynamic viscoelasticity measuring apparatus (VES-F-III, VISCO-ELASTICSPECTROMETER, manufactured by Iwamoto Seisakusho Co., Ltd.), with a temperature distribution mode at a temperature increase rate of 5° C./min, a frequency of 10 Hz, an amplitude of +0.01 mm, to obtain a storage modulus (E'), loss modulus (E"), and loss tangent (tan δ). The temperature of the peak value of the loss tangent (tan δ) of the obtained data was defined as the glass transition temperature.

Table 1 shows the blending formulation and physical properties in Reference Examples.

TABLE 1

| | No. | Reference Example 1 | Reference Example 2 | Reference Example 3 | Reference Example 4 | Reference Example 5 | Reference Example 6 |
|---|---|---|---|---|---|---|---|
| Blending formulation (parts by mass) | Polytetramethylene ether glycol | 100.0 | 100.0 | 100.0 | — | 100.0 | 142.9 |
| | Polycarbonatediol | — | — | — | 100.0 | — | — |
| | 1,3-Propanediol | 2.25 | 2.29 | — | — | — | — |
| | 1,2,6-Hexanetriol | 0.69 | 0.70 | 0.70 | 0.89 | — | — |
| | Neopentyl glycol | — | — | — | — | 4.00 | — |

TABLE 1-continued

|  |  |  | Reference Example 1 | Reference Example 2 | Reference Example 3 | Reference Example 4 | Reference Example 5 | Reference Example 6 |
|---|---|---|---|---|---|---|---|---|
|  | Trimethylolpropane |  | — | — | — | — | 5.00 | — |
|  | 3-Methyl-1,5-pentanediol |  | — | — | — | — | — | 6.55 |
|  | Trimethylolpropane-ethylene oxide adduct |  | — | — | — | — | — | 7.15 |
|  | 2-Ethyl-1-hexanol |  | — | — | — | — | — | 2.32 |
|  | 4,4'-Diphenylmethane diisocyanate |  | 48.75 | 50.85 | 43.00 | 55.25 | 49.80 | 67.70 |
|  | 3,3'-Dimethylbiphenyl-4,4'-diisocyanate |  | — | — | — | — | 14.00 | 18.30 |
|  | 4-Cyano-4'-pentylbiphenyl |  | — | 10 | — | 13.6 | — | — |
|  | 4-Pentylbiphenyl |  | — | — | 10 | — | — | — |
|  | Antioxidant |  | 1 | 1 | 1 | 1 | 1 | 0.2 |
| Physical properties | Photoelastic constant(25° C.) | $\times 10^{-12}$ $Pa^{-1}$ | 5210 | 6110 | 5170 | 6200 | 6280 | 6700 |
|  | Young's modulus(25° C.) | MPa | 5.04 | 3.94 | 4.18 | 3.99 | 5.69 | 3.32 |
|  | Glass transition temperature | ° C. | −5 | −10 | −20 | 25 | 19 | 7 |

(Temperature Dependency of Photoelastic Constant)

The photoelastic constant at 20° C., 35° C., and 40° C. of the molded article 4 (glass transition temperature: 25° C.) obtained in Reference Example 4 was measured. The results are shown in Table 2.

TABLE 2

| Temperature (° C.) | Photoelastic constant ($\times 10^{-12}$ $Pa^{-1}$) |
|---|---|
| 20 | 6320 |
| 35 | 6060 |
| 40 | 5160 |

(Consideration)

The decrease in the photoelastic constant was about 18% at the temperature increase from 20° C. to 40° C., and the change in the photoelastic constant to this extent is considered to have no significant effect on measurement.

Furthermore, the molded articles 1 to 3 and 5 to 6 having variously different glass transition temperatures were measured in the same manner as described above. Similarly to the molded article 4, almost no changes in the photoelastic constant was confirmed from 20° C. to 40° C.

Reference Examples 7 to 11 (Production of Resin Sheets 7 to 11)

The resin sheets 7 to 11 were produced in the same manner as in Reference Example 1. The produced resin sheet was subjected to measurements of the photoelastic constant (25° C.), the Young's modulus (25° C.), and the glass transition temperature.

Reference Examples 12 to 14 (Production of Resin Sheets 12 to 14)

The resin sheets 12 to 14 were produced in the same manner as in Reference Example 1. The produced resin sheet was subjected to measurements of the photoelastic constant (25° C.), the Young's modulus (25° C.), and the glass transition temperature.

In these Reference Examples, dioctyl phthalate (dioctylphthalate, DOP) was added as a plasticizer.

Reference Examples 15 to 17 (Production of Resin Sheets 15 to 17)

The resin sheets 15 to 17 were produced in the same manner as in Reference Example 1. The produced resin sheet was subjected to measurements of the photoelastic constant (25° C.), the Young's modulus (25° C.), and the glass transition temperature.

In these Reference Examples, 2-ethyl-1-hexanol was added as monol.

Evaluation

<Photoelastic Constant and Young's Modulus>

Measurement was conducted in accordance with description of "photoelastic constant measurement method" in "development of a system for measuring the photoelastic constants of optical films" in Journal of The Japan Society for Precision Engineering vol. 73, 253-258 (2007) by Mitsuo Tuskiji, Hiroyuki Takada, and Yoshiro Tajitsu" to obtain distortion optical constant at 25° C. and Young's modulus, and photoelastic constant at 25° C. was calculated therefrom. For the above-described measurement, laser light having a wavelength of 630 nm was used.

<Dynamic Viscoelasticity>

A sample piece was cut into a strip of a length of 2.5 cm, a width of 5.0 mm, and a thickness of 2.0 mm. The sample was measured using a dynamic viscoelasticity measuring apparatus (VES-F-III, VISCO-ELASTICSPECTROMETER, manufactured by Iwamoto Seisakusho Co., Ltd.), with a temperature distribution mode at a temperature increase rate of 5° C./min, a frequency of 10 Hz, an amplitude of ±0.01 mm, to obtain a storage modulus (E'), loss modulus (E"), and loss tangent (tan δ). The temperature of the peak value of the loss tangent (tan δ) of the obtained data was defined as the glass transition temperature.

The tan δ with the measurement frequency of 0.1 and 1 Hz was measured at 32° C. for evaluation of resilience.

The larger the numeral value for tan δ with a low frequency (about 0.1 to 1 Hz) in dynamic viscoelasticity test, the smaller the resilience from the cushioning material to the human body.

<Load Test>

The detection method 1 was used and from a center portion of the end face of a resin sheet having a thickness of 2 mm, sides of 5 cm, a ray of red laser light (wavelength 650 nm) was applied in the sheet, a weight of 10 g was placed at the center of the sheet (on the optical path of the ray of laser light) to cause birefringence, and the intensity of light detected after the light passed through the analyzer was defined as "light intensity".

The spread angle of the detected light was measured, and the angle at which the light intensity decreased to ½ was defined as "half-width". When the half-width is more than 4 degrees, the light spreads while propagating through the resin, and the intensity of light detected may be reduced.

The time taken from removing the load placed on the resin sheet to when the light intensity is reduced to 50% or less was defined as "half time".

<Comfort in Sleeping>

The resin sheet was laminated on the cushioning material (material: soft urethane foam, thickness: 20 cm), and comfort in sleeping when lying on the resin sheet was evaluated based on the following criteria.

Excellent
Good
Slightly hard

Details of the abbreviations in Tables are shown below.

PTG-1000SN: trade name PTG-1000SN, polytetramethylene ether glycol, manufactured by Hodogaya Chemical Co., Ltd., hydroxyl number 111.5 mgKOH/g PTG-650SN: trade name PTG-650SN, polytetramethylene ether glycol, manufactured by Hodogaya Chemical Co., Ltd., hydroxyl number 174.9 mgKOH/g (Consideration)

Comparing Reference Example 7 with Reference Examples 8 to 17, it shows that when the resin has a Tg of −25° C. or less, the half-width is 3.2 degrees or less, and the

TABLE 3

| | No. | | Reference Example 7 | Reference Example 8 | Reference Example 9 | Reference Example 10 | Reference Example 11 | Reference Example 12 |
|---|---|---|---|---|---|---|---|---|
| Blending formulation (parts by mass) | PTG-1000SN | | — | 100 | 43 | 43 | 100 | — |
| | PTG-650SN | | 100 | — | 57 | 57 | — | 100 |
| | 2-Ethyl-1-hexanol | | — | — | — | — | — | — |
| | 3-Methyl-1,5-pentanediol | | — | 3.57 | — | — | — | — |
| | 1,2,6-Hexanetriol | | 0.41 | 0.41 | 0.41 | 0.29 | 0.41 | 0.41 |
| | 4,4'-Diphenylmethane diisocyanate | | 39.9 | 35.3 | 34.4 | 34.1 | 27.3 | 39.9 |
| | Antioxidant | | 0.2 | 0.2 | 0.2 | 0.2 | 0.2 | 0.2 |
| | Plasticizer | | — | — | — | — | — | 15 |
| | Aromatic ring concentration(mass %) | | 17.7 | 15.8 | 15.9 | 15.8 | 13.3 | 16 |
| Evaluation | Photoelasticity | Photoelastic constant ($10^{-12}$ $Pa^{-1}$) | 4680 | 3870 | 3900 | 3960 | 3550 | 4000 |
| | | Young's modulus(MPa) | 4.47 | 4.64 | 4.89 | 4.95 | 4.84 | 4.49 |
| | Dynamic viscoelasticity | Storage modulus(MPa) | 5.78 | 5.70 | 5.76 | 5.69 | 5.81 | 5.23 |
| | | Loss modulus(MPa) | 0.152 | 0.136 | 0.151 | 0.121 | 0.132 | 0.125 |
| | | tanδ(25° C.) | 0.026 | 0.024 | 0.026 | 0.021 | 0.023 | 0.024 |
| | | Glass transition temperature(° C.) | −17 | −26 | −26 | −27 | −36 | −25 |
| | Resilience | tanδ(32° C.) 0.1 Hz | 0.019 | — | — | 0.020 | 0.021 | — |
| | | tanδ(32° C.) 1 Hz | 0.019 | — | — | 0.019 | 0.021 | — |
| | Load test | Light intensity(μW) | 6.9 | 22.6 | 35.6 | 61.6 | 12.0 | 47.9 |
| | | Half-width(deg) | 4.3 | 2.4 | 2.9 | 3.0 | 3.2 | 3.1 |
| | | Half time(sec) | 0 | 0 | 0 | 0 | 0 | 0 |
| | Comfort in sleeping | | — | Slightly hard | Good | Good | Good | Good |

| | No. | | Reference Example 13 | Reference Example 14 | Reference Example 15 | Reference Example 16 | Reference Example 17 |
|---|---|---|---|---|---|---|---|
| Blending formulation (parts by mass) | PTG-1000SN | | 100 | 100 | 100 | 100 | 100 |
| | PTG-650SN | | — | — | — | — | — |
| | 2-Ethyl-1-hexanol | | — | — | 0.29 | 0.36 | 0.43 |
| | 3-Methyl-1,5-pentanediol | | — | — | — | — | — |
| | 1,2,6-Hexanetriol | | 0.41 | 0.41 | 0.41 | 0.41 | 0.41 |
| | 4,4'-Diphenylmethane diisocyanate | | 27.3 | 27.3 | 27.6 | 27.7 | 27.7 |
| | Antioxidant | | 0.2 | 0.2 | 0.2 | 0.2 | 0.2 |
| | Plasticizer | | 5 | 10 | — | — | — |
| | Aromatic ring concentration(mass %) | | 12.8 | 12.4 | 13.4 | 13.4 | 13.4 |
| Evaluation | Photoelasticity | Photoelastic constant ($10^{-12}$ $Pa^{-1}$) | 3420 | 3340 | 3310 | 3130 | 3340 |
| | | Young's modulus(MPa) | 4.05 | 3.4 | 3.02 | 2.78 | 2.17 |
| | Dynamic viscoelasticity | Storage modulus(MPa) | 5.23 | 4.85 | 5.27 | 4.88 | 4.57 |
| | | Loss modulus(MPa) | 0.166 | 0.233 | 0.395 | 0.41 | 0.464 |
| | | tanδ(25° C.) | 0.032 | 0.048 | 0.075 | 0.084 | 0.102 |
| | | Glass transition temperature(° C.) | −38 | −40 | −36 | −37 | −37 |
| | Resilience | tanδ(32° C.) 0.1 Hz | — | — | 0.122 | 0.155 | 0.204 |
| | | tanδ(32° C.) 1 Hz | — | — | 0.107 | 0.126 | 0.158 |
| | Load test | Light intensity(μW) | 10.8 | 20.6 | 36.6 | 68.6 | 40.2 |
| | | Half-width(deg) | 2.8 | 2.6 | 2.9 | 2.8 | 2.6 |
| | | Half time(sec) | 0 | 0 | 5.6 | 10.9 | 18.4 |
| | Comfort in sleeping | | — | Good | Good | Excellent | Excellent | Excellent | detected light does not easily spread, and therefore detection sensitivity of the load is more excellent.

That is, in Reference Examples 8 to 17, the resin has a Tg of −25° C. or less, and a photoelastic constant of $4000\times10^{-12}$ $Pa^{-1}$ or less. When these conditions are satisfied, the half-width of the detected light is sufficiently narrower than 4 degrees, and the laser light does not easily spread in the resin.

The comfort in sleeping was evaluated with three criteria of EXCELLENT, GOOD, and SLIGHTLY HARD. There is a tendency that the smaller the resilience from the cushioning material to the human body, the better the comfort in sleeping when a human body is lying on the cushioning material. In particular, when monol is added to the material composition (Reference Example 15 to 17), the evaluation result was the best.

Meanwhile, in Reference Example 7, in which the Tg is more than −25° C., and the photoelastic constant is more than $4000\times10^{-12}$ $Pa^{-1}$, comfort in sleeping was evaluated as slightly hard. This is probably because the aromatic ring concentration of the resin is slightly high, and the resin is slightly hard.

Regarding the half time, with Reference Examples 15, 16, and 17, in which monol is contained in the material composition, the half time is longer when compared with Reference Example 11. This shows that the light intensity of 50% or more of when the load is placed is obtained within a predetermined period of time even if the load is absent. That is, it can be considered that a sort of memory effects is present.

Using such effects, weight movement on the bed of the person lying on the bed can be determined by measuring light intensity intermittently with a certain interval even if the light intensity is not measured constantly all the time.

For example, by shutting down electricity to the LED and the photodiode usually, and supplying electricity only for, for example, 1 second after every 5 seconds to measure the load, electric consumption can be saved to ⅕. Because the half time is 5 seconds or more, the change in the load can be detected by one measurement for every 5 seconds.

In this manner, when a battery is used for electricity, the time before changing the battery can be extended to 5 times.

It can be assumed that under conditions with a relatively low frequency (0.1 to 1 Hz), in Reference Examples 15 to 17, the value of tan δ is more than 0.1, the resilience felt by the human body is reduced due to the effects of the resin viscosity. This can be considered as one of the reasons for the Excellency of the evaluation results.

While the illustrative embodiments of the present invention are provided in the above description, such is for illustrative purpose only and it is not to be construed restrictively. Modification and variation of the present invention that will be obvious to those skilled in the art is to be covered by the following claims.

INDUSTRIAL APPLICABILITY

The cushioning material having a sensor of the present invention is suitably used for various industrial fields in which pressure detection is required, for example, for a bed, sofa, chair, and seat.

The invention claimed is:

1. A cushioning material having a sensor, comprising:
a resin sheet composed of photoelastic resin,
a cushioning material laminated on the resin sheet,
a photosensor including a light generating unit and a light receiving unit that receives light generated from the light generating unit through the resin sheet, and
a processor that detects a stress applied to the resin sheet based on a light signal detected by the photosensor,
wherein the photoelastic resin has a glass transition temperature less than −25° C.

2. The cushioning material having a sensor according to claim 1, wherein
the light generating unit and the light receiving unit are disposed so as to overlap with the resin sheet on a plane of projection projected in a direction perpendicular to the thickness direction of the resin sheet.

3. The cushioning material having a sensor according to claim 1, wherein
the light generating unit is disposed so as to overlap with the resin sheet on a plane of projection projected in a direction perpendicular to the thickness direction of the resin sheet, and
the light receiving unit is disposed so as to overlap with the resin sheet on a plane of projection projected in the thickness direction of the resin sheet.

4. The cushioning material having a sensor according to claim 3, wherein
the cushioning material has a protruded accommodation unit for accommodating the light receiving unit.

5. The cushioning material having a sensor according to claim 1, wherein
the photoelastic resin has a photoelastic constant at 25° C. of $1000\times10^{-12}$ $Pa^{-1}$ or more and $100000\times10^{-12}$ $Pa^{-1}$ or less.

6. The cushioning material having a sensor according to claim 1, wherein
the photoelastic resin has a glass transition temperature of −60° C. or more.

7. The cushioning material having a sensor according to claim 1, wherein
the photoelastic resin has a Young's modulus at 25° C. of 2 MPa or more and 5 MPa or less.

8. The cushioning material having a sensor according to claim 1, wherein
the photoelastic resin is polyurethane resin.

9. The cushioning material having a sensor according to claim 1, wherein
the photoelastic resin is produced from a polyurethane resin composition containing a polyisocyanate component and an active hydrogen group-containing component,
the polyisocyanate component contains an aromatic ring-containing polyisocyanate having a 1,4-phenylene group, in which a portion of the hydrogen atoms may be replaced with a methyl group and/or a methoxy group, and/or a 1,5-naphthylene group, and
the active hydrogen group-containing component contains a high-molecular weight polyol having an average hydroxyl number of 20 to 500 mgKOH/g.

10. The cushioning material having a sensor according to claim 9, wherein
the active hydrogen group-containing component further contains monol.

11. A bed comprising the cushioning material having a sensor according to claim 1.

* * * * *